(12) United States Patent
Wang et al.

(10) Patent No.: US 9,144,598 B2
(45) Date of Patent: Sep. 29, 2015

(54) REVERSE THERMAL GELS AND THEIR USE IN CELL THERAPY

(71) Applicants: Yadong Wang, Allison Park, PA (US); Martin Oudega, Pittsburgh, PA (US)

(72) Inventors: Yadong Wang, Allison Park, PA (US); Martin Oudega, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/459,178

(22) Filed: Aug. 13, 2014

(65) Prior Publication Data

US 2014/0348778 A1 Nov. 27, 2014

Related U.S. Application Data

(63) Continuation-in-part of application No. 13/581,518, filed as application No. PCT/US2011/027233 on Mar. 4, 2011.

(60) Provisional application No. 61/865,953, filed on Aug. 14, 2013, provisional application No. 61/426,514, filed on Dec. 23, 2010, provisional application No. 61/389,491, filed on Oct. 4, 2010, provisional application No. 61/310,874, filed on Mar. 5, 2010.

(51) Int. Cl.
*A61K 47/48* (2006.01)
*A61K 38/18* (2006.01)
*A61K 35/28* (2015.01)

(52) U.S. Cl.
CPC ............... *A61K 38/185* (2013.01); *A61K 35/28* (2013.01)

(58) Field of Classification Search
None
See application file for complete search history.

(56) References Cited

U.S. PATENT DOCUMENTS

| 6,004,573 | A | 12/1999 | Rathi et al. |
| 6,306,821 | B1 | 10/2001 | Mikos et al. |
| 6,316,011 | B1 | 11/2001 | Ron et al. |
| 6,451,346 | B1 | 9/2002 | Shah et al. |
| 6,541,033 | B1 | 4/2003 | Shah |
| 6,863,859 | B2 | 3/2005 | Levy |
| 2006/0280718 | A1 | 12/2006 | Roy et al. |
| 2008/0274190 | A1 | 11/2008 | Lee et al. |

OTHER PUBLICATIONS

Akdemir, et al. "Photopolymerized Injectable RGD-Modified Fumarated Poly (ethylene glycol) Diglycidyl Ether Hydrogels for Cell Growth." *Macromolecular bioscience* 8, No. 9 (2008): 852-862.
Alferiev, et al. "Prevention of polyurethane valve cusp calcification with covalently attached bisphosphonate diethylamino moieties." *Journal of Biomedical Materials Research Part A* 66, No. 2 (2003): 385-395.
Barakat, et al. "VEGF inhibitors for the treatment of neovascular age-related macular degeneration." *Healthcare Expert Opinion* (2009): 637-646.
Burdick, et al. "Stimulation of neurite outgrowth by neurotrophins delivered from degradable hydrogels." *Biomaterials* 27, No. 3 (2006): 452-459.
Chappelow, et al. "Neovascular age-related macular degeneration." *Drugs* 68, No. 8 (2008): 1029-1036.
Chen, et al. "Preparation and evaluation of thermo-reversible copolymer hydrogels containing chitosan and hyaluronic acid as injectable cell carriers." *Polymer* 50, No. 1 (2009): 107-116.
Choi, et al. "Thermoreversible gelation of poly (ethylene oxide) biodegradable polyester block copolymers. Ii." *Journal of Polymer Science Part A Polymer Chemistry* 37 (1999): 2207-2218.
Christenson, et al. "Enzymatic degradation of poly (ether urethane) and poly (carbonate urethane) by cholesterol esterase." *Biomaterials* 27, No. 21 (2006): 3920-3926.
Christenson, et al. "Oxidative mechanisms of poly (carbonate urethane) and poly (ether urethane) biodegradation: in vivo and in vitro correlations." *Journal of Biomedical Materials Research Part A* 70, No. 2 (2004): 245-255.
Chun, et al. "The use of injectable, thermosensitive poly (organophosphazene)—RGD conjugates for the enhancement of mesenchymal stem cell osteogenic differentiation." Biomaterials 30, No. 31 (2009): 6295-6308.
Cohn, et al. "PEO—PPO—PEO-based poly (ether ester urethane)s as degradable reverse thermo-responsive multiblock copolymers." *Biomaterials* 27, No. 9 (2006): 1718-1727.
Dayananda, et al. "pH-and temperature-sensitive multiblock copolymer hydrogels composed of poly (ethylene glycol) and poly (amino urethane)." *Polymer* 49, No. 23 (2008): 4968-4973.
D'Errico, et al. "Structural and mechanical properties of UV photocrosslinked poly (N-vinyl-2-pyrrolidone) hydrogels." *Biomacromolecules* 9, No. 1 (2008): 231-240.

(Continued)

*Primary Examiner* — Amber D Steele
*Assistant Examiner* — Schuyler Milton
(74) *Attorney, Agent, or Firm* — Klarquist Sparkman, LLP

(57) ABSTRACT

Methods are disclosed herein for increasing survival of transplanted cells, either in vitro or in vivo. In additional embodiments, methods are disclosed for treating a subject with a spinal cord injury or a neurodegenerative disorder. The methods include administering to a subject a therapeutically effective amount of cells, such as bone marrow stromal cells, and a therapeutically effective amount of a reverse thermal gel composition. The reverse thermal gel compositing includes a triblock copolymer, or pharmaceutically acceptable salt thereof, having the structure B-A-B in which A is one of a polyurethane or poly(ester urethane) group that comprises one or more pendant active groups, blocked active groups or active agents and B is a hydrophilic block, wherein the composition is a gel at 25° C.-40° C. and a liquid solution at a lower temperature.

31 Claims, 20 Drawing Sheets

(56) References Cited

OTHER PUBLICATIONS

Eglin, et al. "Farsenol-modified biodegradable polyurethanes for cartilage tissue engineering." *Journal of Biomedical Materials Research Part A* 92, No. 1 (2010): 393-408.
Fairbanks, et al. "Photoinitiated polymerization of PEG-diacrylate with lithium phenyl-2, 4, 6-trimethylbenzoylphosphinate: polymerization rate and cytocompatibility." *Biomaterials* 30, No. 35 (2009): 6702-6707.
Gao, et al. "A neuroinductive biomaterial based on dopamine." *Proceedings of the National Academy of Sciences* 103, No. 45 (2006): 16681-16686.
Gorna, et al. "Preparation, degradation, and calcification of biodegradable polyurethane foams for bone graft substitutes." *Journal of Biomedical Materials Research Part A* 67, No. 3 (2003): 813-827.
Gou, et al. "A novel injectable local hydrophobic drug delivery system: biodegradable nanoparticles in thermo-sensitive hydrogel." *International Journal of Pharmaceutics* 359, No. 1 (2008): 228-233.
Hacker, et al. "Synthesis and characterization of injectable, thermally and chemically gelable, amphiphilic poly (N-isopropylacrylamide)-based macromers." *Biomacromolecules* 9, No. 6 (2008): 1558-1570.
He, et al. "In situ gelling stimuli-sensitive block copolymer hydrogels for drug delivery." *Journal of Controlled Release* 127, No. 3 (2008): 189-207.
Heller, et al. "Patterned networks of mouse hippocampal neurons on peptide-coated gold surfaces." *Biomaterials* 26, No. 8 (2005): 883-889.
Hiratani, et al. "Ocular release of timolol from molecularly imprinted soft contact lenses." *Biomaterials* 26, No. 11 (2005): 1293-1298.
Hou, et al. "In situ gelling hydrogels incorporating microparticles as drug delivery carriers for regenerative medicine." *Journal of Pharmaceutical Sciences* 97, No. 9 (2008): 3972-3980.
Huynh, et al. "Functionalized injectable hydrogels for controlled insulin delivery." *Biomaterials* 29, No. 16 (2008): 2527-2534.
Iso Inside, "Biological evaluation of medical devices—Part 5: Tests for in vitro cytotoxicity." *NSAI Standards Irish Standard LS_EN ISO 10993-5*, (2009) 16 pages.
Jeong, et al. "Biodegradable block copolymers as injectable drug-delivery systems." *Nature* 388, No. 6645 (1997): 860-862.
Jeong, et al. "Thermoreversible gelation of poly (ethylene oxide) biodegradable polyester block copolymers." *Journal of Polymer Science Part A: Polymer Chemistry* 37, No. 6 (1999): 751-760.
Jeong, et al. "Thermosensitive sol—gel reversible hydrogels." *Advanced drug delivery reviews* 54, No. 1 (2002): 37-51.
Jo, et al. "Reverse thermal gelation of aliphatically modified biodegradable triblock copolymers." *Macromolecular bioscience* 6, No. 11 (2006): 923-928.
Johnston, et al.. "Sustained delivery of interleukin-2 from a poloxamer 407 gel matrix following intraperitoneal injection in mice." *Pharmaceutical Research* 9, No. 3 (1992): 425-434.
Jun, et al. "In situ gel forming stereocomplex composed of four-arm PEG-PDLA and PEG-PLLA block copolymers." *Macromolecular Research* 16, No. 8 (2008): 704-710.
JungáChung, et al. "Thermo-sensitive, injectable, and tissue adhesive sol—gel transition hyaluronic acid/pluronic composite hydrogels prepared from bio-inspired catechol-thiol reaction." *Soft Matter* 6, No. 5 (2010): 977-983. (Previously listed as Lee, et al.).
Justin, Gusphyl, and Anthony Guiseppi-Elie. "Characterization of electroconductive blends of poly (HEMA-co-PEGMA-co-HMMA-co-SPMA) and poly (Py-co-PyBA)." *Biomacromolecules* 10, No. 9 (2009): 2539-2549.
Khorasani, et al. "Fabrication of microporous thermoplastic polyurethane for use as small-diameter vascular graft material. I. Phase-inversion method." *Journal of Biomedical Materials Research Part B: Applied Biomaterials* 76, no. 1 (2006): 41-48.
Kim, et al. "Injectable in situ-forming pH/thermo-sensitive hydrogel for bone tissue engineering." *Tissue Engineering Part A* 15, No. 4 (2008): 923-933.
Kim, et al. "Reverse thermal gelling PEG-PTMC diblock copolymer aqueous solution." *Macromolecules* 40, No. 15 (2007): 5519-5525.
Lee, et al. "Novel thermoreversible gelation of biodegradable PLGA-block-PEO-block-PLGA triblock copolymers in aqueous solution." *Macromolecular Rapid Communications* 22, No. 8 (2001): 587-592.
Lin, et al. "Functional PEG—peptide hydrogels to modulate local inflammation inducedby the pro-inflammatory cytokine TNFα." *Biomaterials* 30, No. 28 (2009): 4907-4914.
Lu, et al. "Pharmacokinetic studies of methotrexate in plasma and synovial fluid following iv bolus and topical routes of administration in dogs." *Pharmaceutical Research* 12, No. 10 (1995): 1474-1477.
Mahoney, et al. "Three-dimensional growth and function of neural tissue in degradable polyethylene glycol hydrogels." *Biomaterials* 27, No. 10 (2006): 2265-2274.
Mann, et al. "Smooth muscle cell growth in photopolymerized hydrogels with cell adhesive and proteolytically degradable domains: synthetic ECM analogs for tissue engineering." *Biomaterials* 22, No. 22 (2001): 3045-3051.
Mann, et al. "Tethered-TGF-β increases extracellular matrix production of vascular smooth muscle cells." *Biomaterials* 22, No. 5 (2001): 439-444.
Matsuda, et al. "A polyurethane vascular access graft and a hybrid polytetrafluoroethylene graft as an arteriovenous fistula for hemodialysis: Comparison with an expanded polytetrafluoroethylene graft." *Artificial Organs* 27, No. 8 (2003): 722-727.
McBane, et al. "The interaction between hydrolytic and oxidative pathways in macrophage-mediated polyurethane degradation." *Journal of Biomedical Materials Research Part A* 82, No. 4 (2007): 984-994.
McLemore, et al. "Controlling delivery properties of a waterborne, in-situ-forming biomaterial." *Journal of Biomedical Materials Research Part B: Applied Biomaterials* 79, No. 2 (2006): 398-410.
Miller, et al. "Bioactive hydrogels made from step-growth derived PEG—peptide macromers." *Biomaterials* 31, No. 13 (2010): 3736-3743.
Nguyen, et al. "Injectable Poly (amidoamine)-poly (ethylene glycol)-poly (amidoamine) Triblock Copolymer Hydrogel with Dual Sensitivities: pH and Temperature." *Biomacromolecules* 10, No. 4 (2009): 728-731.
Obara, et al. "Controlled release of paclitaxel from photocrosslinked chitosan hydrogels and its subsequent effect on subcutaneous tumor growth in mice." *Journal of Controlled Release* 110, No. 1 (2005): 79-89.
Ogura, et al. "Preparation and solution behavior of a thermoresponsive diblock copolymer of poly (ethyl glycidyl ether) and poly (ethylene oxide)." *Langmuir* 23, No. 18 (2007): 9429-9434.
Oh, et al. "Secondary structure effect of polypeptide on reverse thermal gelation and degradation of l/dl-poly (alanine)-poloxamer-l/dl-poly (alanine) copolymers." *Macromolecules* 41, No. 21 (2008): 8204-8209.
Park, et al. "Injectable biodegradable hydrogel composites for rabbit marrow mesenchymal stem cell and growth factor delivery for cartilage tissue engineering." *Biomaterials* 28, No. 21 (2007): 3217-3227.
Park, et al. "PDMS-based polyurethanes with MPEG grafts: Mechanical properties, bacterial repellency, and release behavior of rifampicin." *Journal of Biomaterials Science, Polymer Edition* 12, No. 6 (2001): 629-645.
Rafat, et al. "PEG-stabilized carbodiimide crosslinked collagen-chitosan hydrogels for corneal tissue engineering." *Biomaterials* 29, No. 29 (2008): 3960-3972.
Rickerby, et al. "A biomedical library of serinol-derived polyesters." *Journal of controlled release* 101, No. 1 (2005): 21-34.
Rockwood, et al. "Characterization of biodegradable polyurethane microfibers for tissue engineering." *Journal of Biomaterials Science, Polymer Edition* 18, No. 6 (2007): 743-758.
Sahoo, et al. "Hydrolytically degradable hyaluronic acid hydrogels with controlled temporal structures." *Biomacromolecules* 9, No. 4 (2008): 1088-1092.
Santiago, et al. "Peptide-surface modification of poly (caprolactone) with laminin-derived sequences for adipose-derived stem cell applications." *Biomaterials* 27, No. 15 (2006): 2962-2969.
Sarkar, et al. "Oxidative and enzymatic degradations of L-tyrosine based polyurethanes." *Polymer Degradation and Stability* 92, No. 11 (2007): 1994-2004.

(56) References Cited

OTHER PUBLICATIONS

Sarkar, et al. "Synthesis and characterization of L-tyrosine based polyurethanes for biomaterial applications." *Journal of Biomedical Materials Research Part A* 90, No. 1 (2009): 263-271.

Sartori, et al. "New strategies in polymeric biomaterials functionalization." *European Cells and Materials* 14, Suppl. 3 (2007): 18.

Schubert, et al. "Oxidative biodegradation mechanisms of biaxially strained poly (etherurethane urea) elastomers." *Journal of Biomedical Materials Research* 29, No. 3 (1995): 337-347.

Schubert, et al. "Role of oxygen in biodegradation of poly (etherurethane urea) elastomers." *Journal of Biomedical Materials Research* 34, No. 4 (1997): 519-530.

Shu, Xiao Zheng, et al. "In situ crosslinkable hyaluronan hydrogels for tissue engineering." *Biomaterials* 25, No. 7 (2004): 1339-1348. (Previously listed as Zheng Shu et al.).

Silva, et al. "Selective differentiation of neural progenitor cells by high-epitope density nanofibers." *Science* 303, No. 5662 (2004): 1352-1355.

Smith, et al. "Uptake of drugs by catheters: the influence of the drug molecule on sorption by polyurethane catheters." *Biomaterials* 17, No. 15 (1996): 1469-1472.

Sundback, et al. "Biocompatibility analysis of poly (glycerol sebacate) as a nerve guide material." *Biomaterials* 26, No. 27 (2005): 5454-5464.

Taguchi, et al. "Encapsulation of chondrocytes in injectable alkali-treated collagen gels prepared using poly (ethylene glycol)-based 4-armed star polymer." *Biomaterials* 26, No. 11 (2005): 1247-1252.

Tang, et al. "Biodegradable and biocompatible thermosensitive polymer based injectable implant for controlled release of protein." *International Journal of Pharmaceutics* 365, No. 1 (2009): 34-43.

Tang, et al. "Enzyme induced biodegradation of polycarbonate-polyurethanes: dose dependence effect of cholesterol esterase." *Biomaterials* 24, No. 12 (2003).

Tang, et al. "Enzyme-induced biodegradation of polycarbonate polyurethanes: Dependence on hard-segment concentration." *Journal of Biomedical Materials Research* 56, No. 4 (2001): 516-528.

Tomlinson, et al. "Pendent chain functionalized polyacetals that display pH-dependent degradation: A platform for the development of novel polymer therapeutics." *Macromolecules* 35, No. 2 (2002): 473-480.

Tysseling-Mattiace, et al. "Self-assembling nanofibers inhibit glial scar formation and promote axon elongation after spinal cord injury." *The Journal of Neuroscience* 28, No. 14 (2008): 3814-3823.

Woodhouse, et al. "Investigation of recombinant human elastin polypeptides as non-thrombogenic coatings." *Biomaterials* 25, No. 19 (2004): 4543-4553.

Yao, et al. "The effect of laminin peptide gradient in enzymatically cross-linked collagen scaffolds on neurite growth." *Journal of Biomedical Materials Research Part A* 92, No. 2 (2010): 484-492.

Yeo, et al. "Photocrosslinkable hydrogel for myocyte cell culture and injection." *Journal of Biomedical Materials Research Part B: Applied Biomaterials* 81, No. 2 (2007): 312-322.

Yeom, et al. "Effect of cross-linking reagents for hyaluronic acid hydrogel dermal fillers on tissue augmentation and regeneration." *Bioconjugate Chemistry* 21, No. 2 (2010): 240-247.

Yu, et al. "Peptide surface modification of methacrylamide chitosan for neural tissue engineering applications." *Journal of Biomedical Materials Research Part A* 82, No. 1 (2007): 243-255.

Zdrahala, et al. "Biomedical applications of polyurethanes: A review of past promises, present realities, and a vibrant future." *Journal of Biomaterials Applications* 14, No. 1 (1999): 67-90.

Zhang, et al. "Loading dependent swelling and release properties of novel biodegradable, elastic and environmental stimuli-sensitive polyurethanes." *Journal of Controlled Release* 131, No. 2 (2008): 128-136.

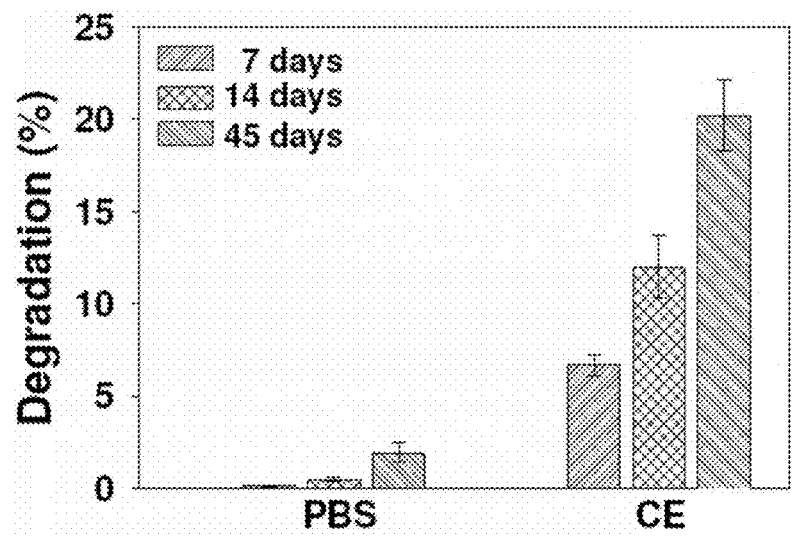
FIG. 10
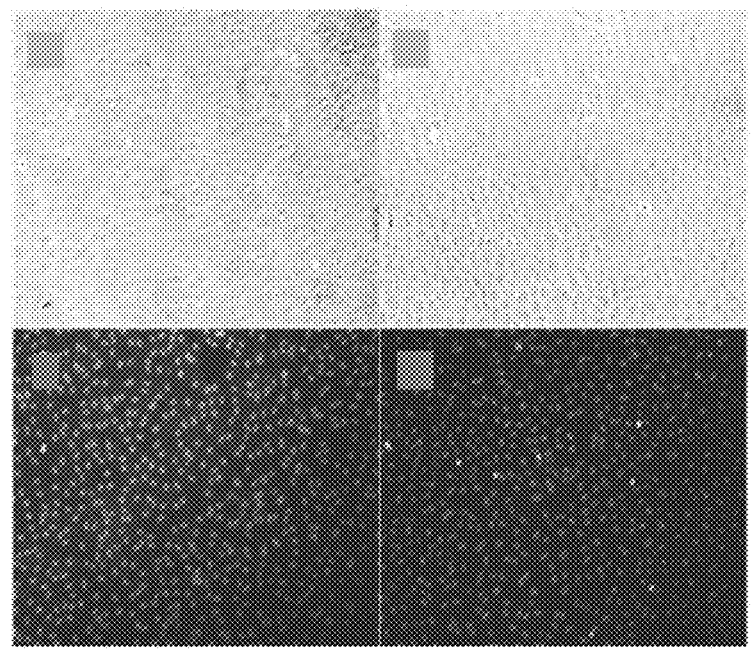
FIG. 11A FIG. 11B
FIG. 11C FIG. 11D

FIG. 15A  FIG. 15B
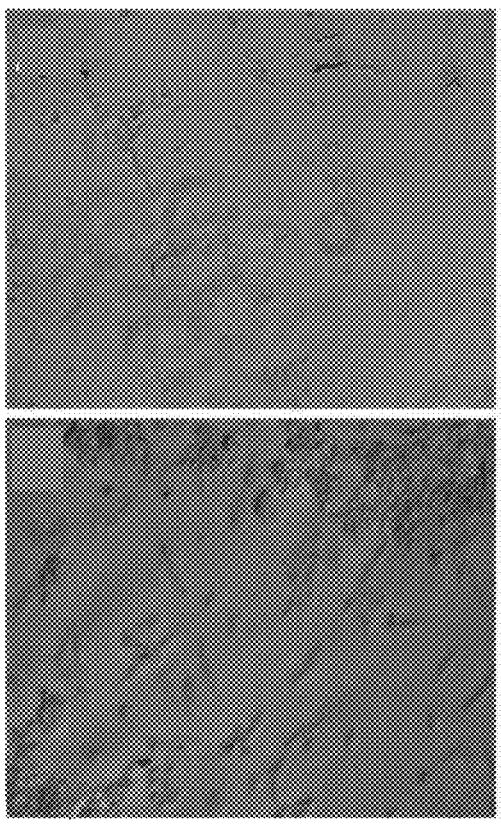 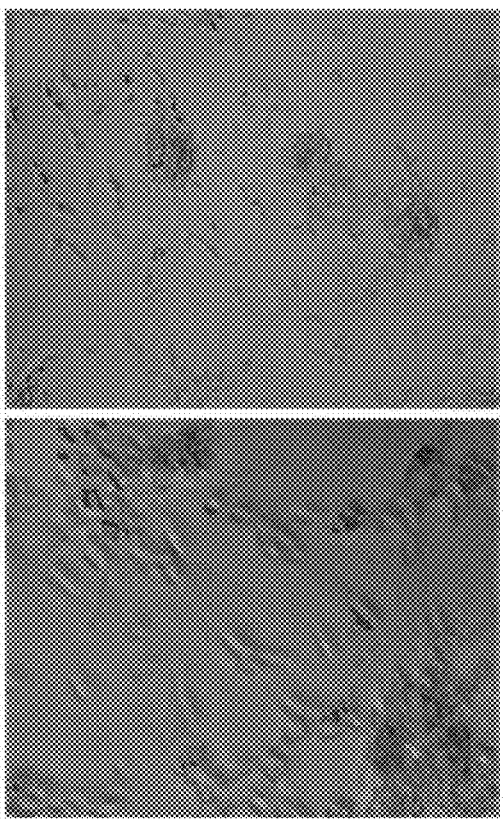
 
FIG. 15C  FIG. 15D FIG. 16A
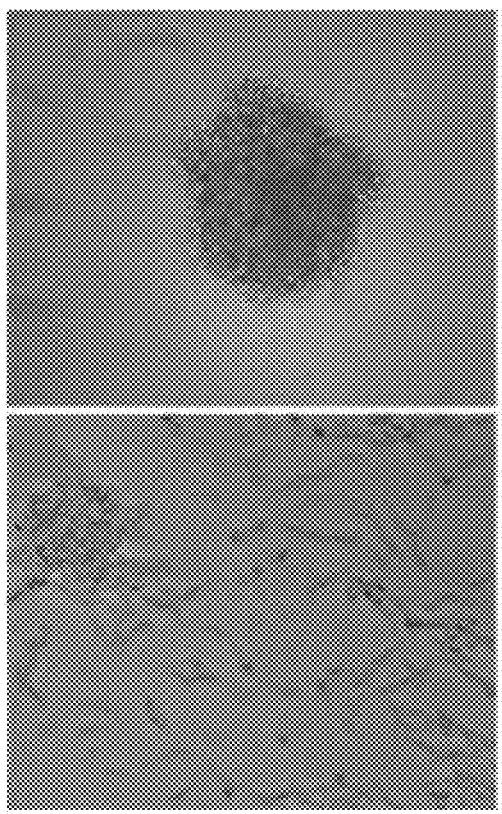
FIG. 16C
FIG. 16B
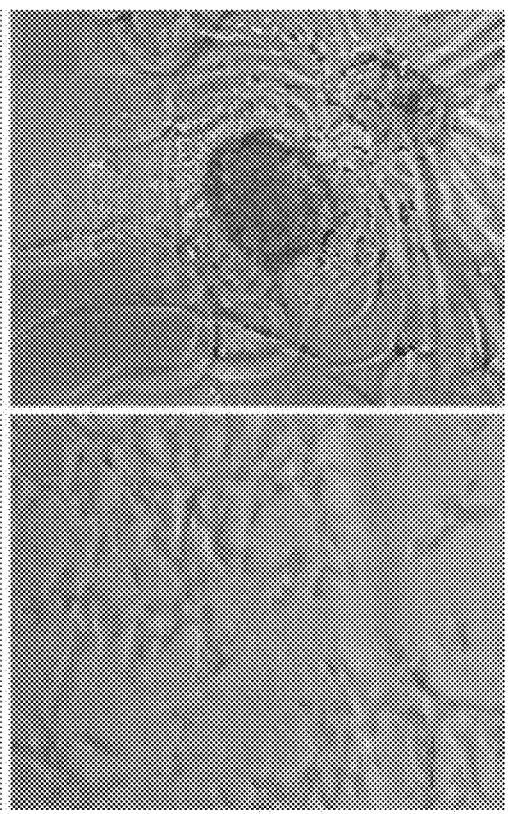
FIG. 16D FIG. 17A  FIG. 17B
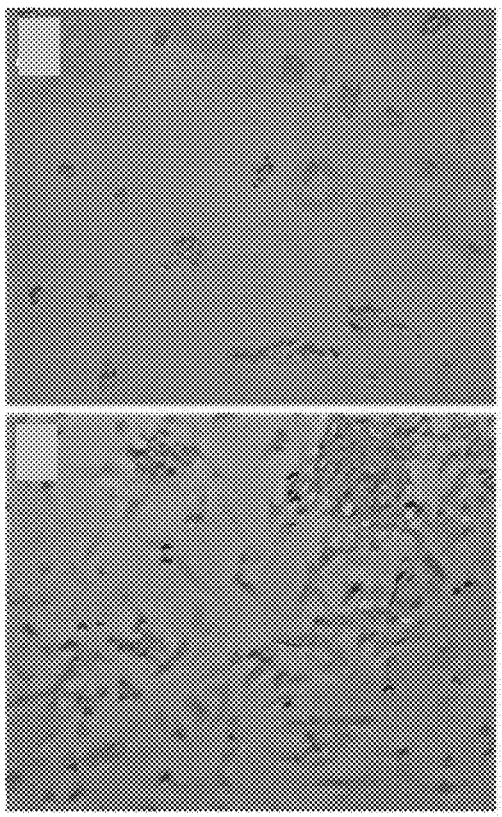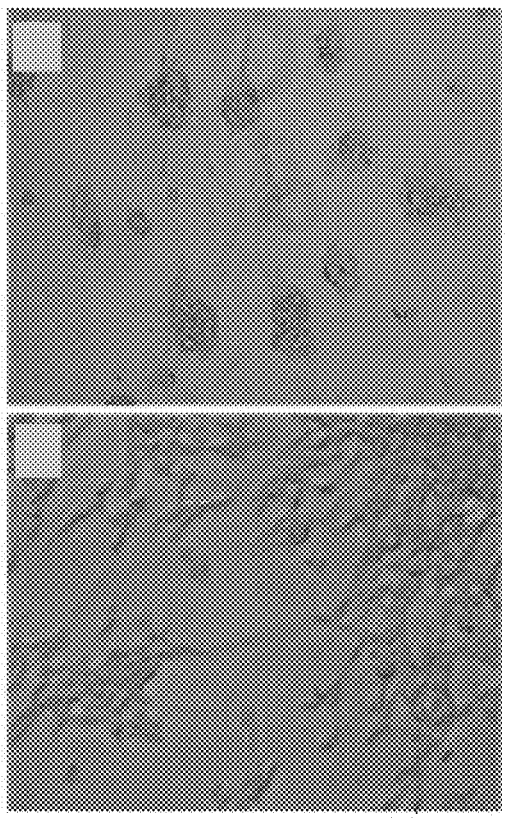
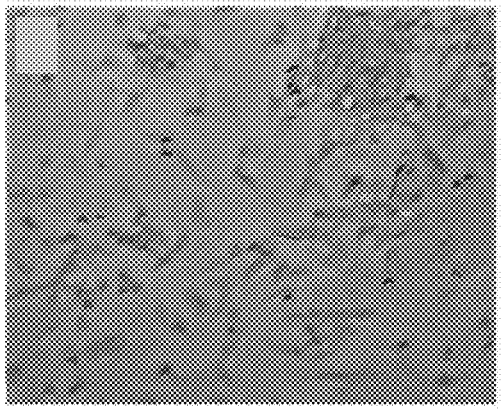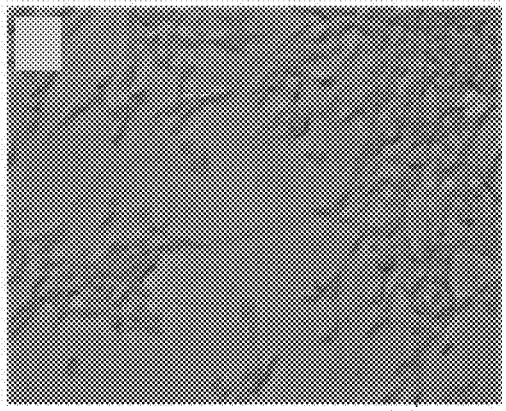
FIG. 17C  FIG. 17D FIG. 20A  FIG. 20B
ESHU  PBS
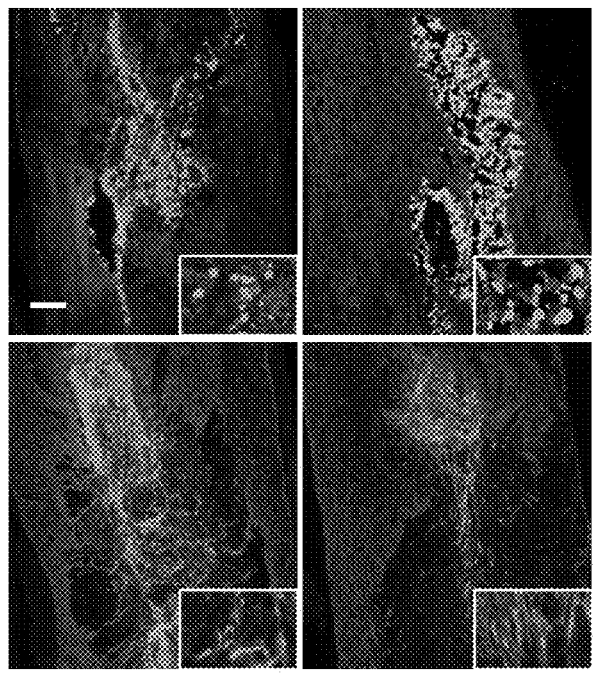
FIG. 20C  FIG. 20D
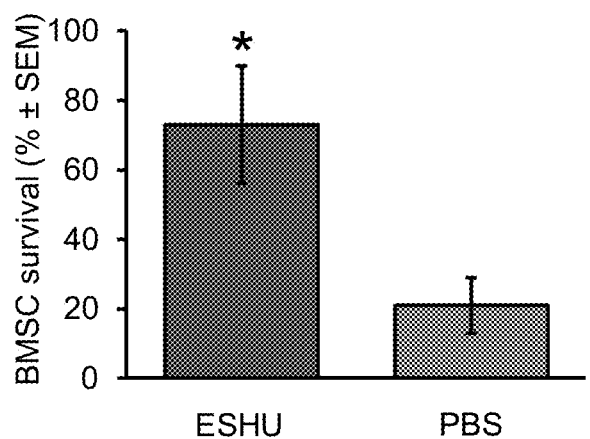
FIG. 20E FIG. 21A  FIG. 22B  FIG. 22C
ED-1    GFP     ED-1/GFP
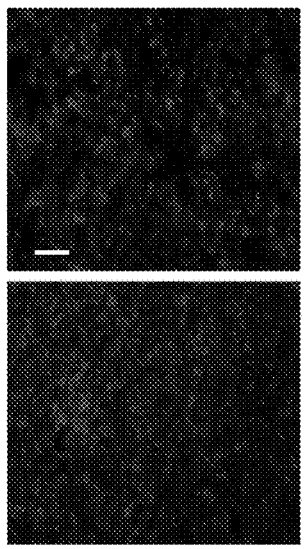
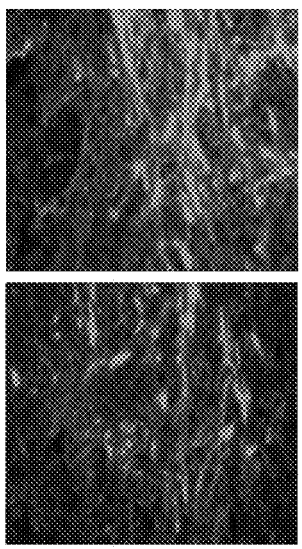
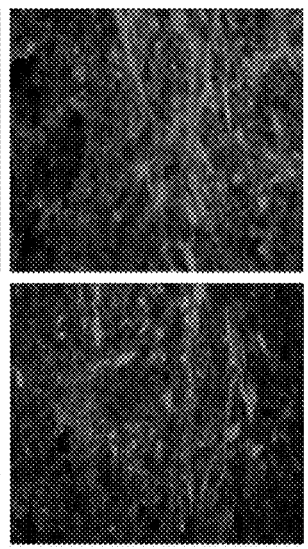
FIG. 21D  FIG. 21E  FIG. 21F
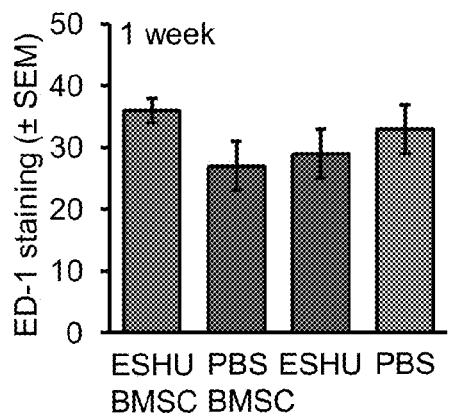
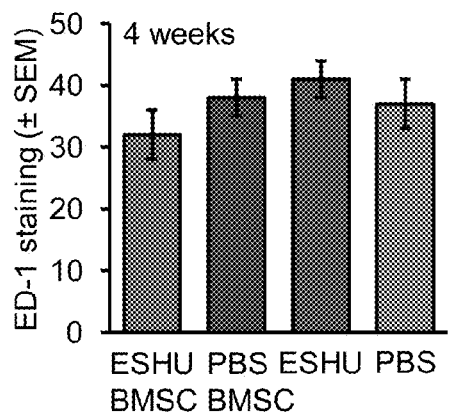
FIG. 21G

SEQUENCE LISTING

```
<160> NUMBER OF SEQ ID NOS: 21

<210> SEQ ID NO 1
<211> LENGTH: 5
<212> TYPE: PRT
<213> ORGANISM: Homo sapiens

<400> SEQUENCE: 1

Ile Lys Leu Leu Ile
1               5

<210> SEQ ID NO 2
<211> LENGTH: 4
<212> TYPE: PRT
<213> ORGANISM: Homo sapiens

<400> SEQUENCE: 2

Arg Glu Asp Val
1

<210> SEQ ID NO 3
<211> LENGTH: 5
<212> TYPE: PRT
<213> ORGANISM: Homo sapiens

<400> SEQUENCE: 3

Arg Gly Asp Ser Pro
1               5

<210> SEQ ID NO 4
<211> LENGTH: 4
<212> TYPE: PRT
<213> ORGANISM: Homo sapiens

<400> SEQUENCE: 4

Arg Gly Asp Val
1

<210> SEQ ID NO 5
<211> LENGTH: 5
<212> TYPE: PRT
<213> ORGANISM: Homo sapiens

<400> SEQUENCE: 5

Leu Arg Gly Asp Asn
1               5

<210> SEQ ID NO 6
<211> LENGTH: 4
<212> TYPE: PRT
<213> ORGANISM: Homo sapiens

<400> SEQUENCE: 6

Arg Gly Asp Thr
1

<210> SEQ ID NO 7
<211> LENGTH: 5
<212> TYPE: PRT
<213> ORGANISM: Homo sapiens

<400> SEQUENCE: 7

Tyr Ile Gly Ser Arg
1               5
```

<210> SEQ ID NO 8
<211> LENGTH: 6
<212> TYPE: PRT
<213> ORGANISM: Homo sapiens

<400> SEQUENCE: 8

Thr Thr Ser Trp Ser Gln
1               5

<210> SEQ ID NO 9
<211> LENGTH: 8
<212> TYPE: PRT
<213> ORGANISM: Homo sapiens

<400> SEQUENCE: 9

Ala Glu Ile Asp Gly Ile Glu Leu
1               5

<210> SEQ ID NO 10
<211> LENGTH: 6
<212> TYPE: PRT
<213> ORGANISM: Homo sapiens

<400> SEQUENCE: 10

Trp Tyr Arg Gly Arg Leu
1               5

<210> SEQ ID NO 11
<211> LENGTH: 7
<212> TYPE: PRT
<213> ORGANISM: Homo sapiens

<400> SEQUENCE: 11

Ser Ile Lys Val Ala Val Ser
1               5

<210> SEQ ID NO 12
<211> LENGTH: 5
<212> TYPE: PRT
<213> ORGANISM: Homo sapiens

<400> SEQUENCE: 12

Pro Asp Ser Gly Arg
1               5

<210> SEQ ID NO 13
<211> LENGTH: 10
<212> TYPE: PRT
<213> ORGANISM: Homo sapiens

<400> SEQUENCE: 13

Arg Asn Ile Ala Glu Ile Ile Lys Asp Ile
1               5                   10

<210> SEQ ID NO 14
<211> LENGTH: 4
<212> TYPE: PRT
<213> ORGANISM: Homo sapiens

<400> SEQUENCE: 14

Asp Gly Glu Ala
1

<210> SEQ ID NO 15

```
<211> LENGTH: 4
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Val Thr Xaa Gly
1

<210> SEQ ID NO 16
<211> LENGTH: 6
<212> TYPE: PRT
<213> ORGANISM: Homo sapiens

<400> SEQUENCE: 16

Pro Arg Arg Ala Arg Val
1               5

<210> SEQ ID NO 17
<211> LENGTH: 19
<212> TYPE: PRT
<213> ORGANISM: Homo sapiens

<400> SEQUENCE: 17

Tyr Glu Lys Pro Gly Ser Pro Pro Arg Glu Val Val Pro Arg Pro Arg
1               5                   10                  15

Pro Gly Val

<210> SEQ ID NO 18
<211> LENGTH: 28
<212> TYPE: PRT
<213> ORGANISM: Homo sapiens

<400> SEQUENCE: 18

Arg Pro Ser Leu Ala Lys Lys Gln Arg Phe Arg His Arg Asn Arg Lys
1               5                   10                  15

Gly Tyr Arg Ser Gln Arg Gly His Ser Arg Gly Arg
            20                  25

<210> SEQ ID NO 19
<211> LENGTH: 17
<212> TYPE: PRT
<213> ORGANISM: Homo sapiens

<400> SEQUENCE: 19

Arg Ile Gln Asn Leu Leu Lys Ile Thr Asn Leu Arg Ile Lys Phe Val
1               5                   10                  15

Lys

<210> SEQ ID NO 20
<211> LENGTH: 5
<212> TYPE: PRT
```

```
<213> ORGANISM: Homo sapiens

<400> SEQUENCE: 20

Ile Lys Val Ala Val
1               5

<210> SEQ ID NO 21
<211> LENGTH: 6
<212> TYPE: PRT
<213> ORGANISM: Homo sapiens

<400> SEQUENCE: 21

Ile Lys Val Ala Val Ser
1               5
```

REVERSE THERMAL GELS AND THEIR USE IN CELL THERAPY

CROSS REFERENCE TO RELATED APPLICATIONS

This claims the benefit of U.S. Patent Application No. 61/865,953, filed Aug. 14, 2013. This is also a continuation-in-part of U.S. patent application Ser. No. 13/581,518, filed Dec. 10, 2012, which is the 371 national stage of PCT/US2011/027233, filed Mar. 4, 2011, which was published in English under Article 21(2) and claims the benefit of U.S. Provisional Application No. 61/426,514, filed Dec. 23, 2010, U.S. Provisional Application No. 61/389,491, filed Oct. 4, 2010, and U.S. Provisional Application No. 61/310,874, filed Mar. 5, 2010. The prior applications are all incorporated herein by reference.

ACKNOWLEDGMENT OF GOVERNMENT SUPPORT

This invention was made with government support under grant no. 5T32EB003392-07 awarded by the National Institutes of Health and grant no. DMR-1206589 awarded by the National Science Foundation. The government has certain rights in the invention.

FIELD OF THE DISCLOSURE

This application relates to the field of cell transplantation for tissue repair, and specifically to the use of reverse thermal gel compositions to promote survival of transplanted cells.

BACKGROUND

Cell transplantation is considered for treatment of a myriad range of ailments including nervous tissue injury, cardiomyopathy, wound healing, and muscle dystrophy. Transplanted cells are chosen because of their reparative proficiency and accessibility. However, transplanted cell survival is often compromised. For instance, bone marrow-derived stromal cells (BMSCs) are often used in tissue repair approaches but they survive poorly in an injury site. In a model of spinal cord injury most BMSCs are lost during the first week post-transplantation. This early loss of BMSC transplants may limit their repair efficacy.

Reactive oxygen species (ROS) present in damaged tissue (Deng et al., *Exp. Neurol.* 205, 154-165 (2007); Bains and Hall, *Biochim. Biophys. Acta* 1822(5), 675-684 (2012); Facchinetti et al., *Cell Mol. Neurobiol.* 18(6), 667-682 (1998); Hamann, K. et al. *J. Neurochem.* 107(3), 712-721 (2008)) cause oxidative stress/damage which contributes to the loss of transplanted cells (Nandoe Tewarie, R. D. et al. *J. Neurotrauma* 26(12), 2313-2322 (2009); Swanger et al., *Cell Transplant.* 14(10), 775-786 (2005); Parr et al., *Surg. Neurol.* 70 (6): 600-607 (2008); Liu, D. et al. Superoxide production after spinal injury detected by microperfusion of cytochrome c. *Free Radic. Biol. Med.* 25, 298-304 (1998); Bao and Liu. *Neurosci.* 126, 285-295 (2004)). Methods that lead to ROS scavenging is a possible therapy to protect transplants from oxidative stress-related loss.

A need remains for methods to increase survival of stem cells, such as bone marrow stem cells.

SUMMARY OF THE DISCLOSURE

Methods are disclosed herein for increasing cell transplant survival. The method includes administering to a subject an effective amount of cells within a therapeutically effective amount of a reverse thermal gel composition comprising a triblock copolymer, or a pharmaceutically acceptable salt thereof, having the structure B-A-B in which A is one of a polyurethane or poly(ester urethane) group that comprises one or more pendant active groups, blocked active groups or active agents and B is a hydrophilic block, wherein the composition is a gel at about 35° C. to about 40° C. and a liquid solution at a lower temperature. In some embodiments, the cell is a bone marrow-derived mesenchymal stem cell. In other embodiments, cells can be administered to the peripheral or the central nervous system. In further embodiments, the methods can result in the decreased production of reaction oxygen species. In additional embodiments, the reverse thermal gel composition comprises poly(ethylene glycol)-poly (serinol hexamethylene urethane).

The foregoing and other features and advantages of the disclosure will become more apparent from the following detailed description of a several embodiments which proceeds with reference to the accompanying figures.

BRIEF DESCRIPTION OF THE FIGURES

FIG. 10. A graph showing in vitro degradation of ESHU in PBS and CE solution. The degradation of ESHU was much faster in the presence of CE. Data are presented as means±S.D (n=3).

FIGS. 11A-11D. In vitro cytotoxicity toward primary bovine corneal endothelium cells. Phase images (100×) of Calcein AM treated cell morphologies of (A) control and (B) ESHU. No differences were observed between control and ESHU. Fluorescence images (100×) of cells of (C) control and (D) ESHU which stained with Hoechst and propidium iodide. Most nuclei (blue dots) are intact with a few red one.

FIGS. 12A-12C provide representative fluorescent photomicrographs (200×, scale bar=60 μm) of injection sites stained for ED1+ macrophages (red in original). Tissues were harvested after: (A) 3 days; (B) 14 days, and (C) 28 days. FIG. 12D is a graph illustrating the number of ED1+ macrophages decreased with time indicating a reduction in inflammatory response. ** $p<0.01$ (paired Student's t-test).

FIGS. 15A-15D. Phase contrast of cell morphology and neurite outgrowth on laminin surface. (A) 1 day, (B) 7 days, (C) 14 days without RA, and (D) 14 days with RA. Images were taken by the magnification of 100× for (A) and (B), and 200× for (C) and (D).

FIGS. 16A-16D. Phase contrast of cell morphology and neurite outgrowth on pure reverse thermal gel surface. (A) 1 day, (B) 7 days, (C) 14 days without RA, and (D) 14 days with RA. Images were taken by the magnification of 100× for (A) and (B), and 200× for (C) and (D).

FIGS. 17A-17D. Phase contrast of cell morphology and neurite outgrowth on IKVAVS-GEL surface. (A) 1 day, (B) 7 days, (C) 14 days without RA, and (D) 14 days with RA. Images were taken by the magnification of 100× for (A) and (B), and 200× for (C) and (D).

FIGS. 20A-20E. ESHU improves the survival of bone marrow stromal cell transplants in a spinal cord contusion. Fifteen minutes after injection, transplanted cells (green) occupied most of the contusion regardless whether they were suspended in ESHU (A) or phosphate-buffered saline (PBS) (B). Staining for glial-fibrillary acidic protein (GFAP, red) was used to outline the contusion. Transplanted cells were mostly rounded in ESHU (insert panel a) and PBS (insert panel b). One week after injection, the transplant occupied only part of the contusion site but more so when suspended in ESHU (C) than PBS (D). The transplanted cells at this time point were mostly elongated with bipolar morphologies in ESHU (insert panel C) and PBS (insert panel D). (E) Bar graph showing that more transplanted cells survive in the contusion site the first week after injection when suspended in ESHU than PBS. Survival rate was measured against total number of injected cells. Error bars in bar graph display standard error of the mean (SEM) and asterisk indicates $p<0.05$. Bar in a=350 μm in FIGS. 20A-20D and 30 μm in inserts.

FIGS. 21A-21G. ESHU does not affect the injury-induced macrophage response. Macrophages (ED-$1^+$, red) were found in the contusion at one (A) and four (D) weeks after transplantation of bone marrow stromal cells (green) in ESHU (B) or PBS (E). Macrophages and transplanted cells are shown in (c, one week after injection) and (F, four weeks after injection). (G) Bar graph showing that ESHU as a transplant matrix or alone did not affect the presence of macrophages in the contusion at one and four weeks after transplantation. Error bars in bar graphs display standard error of the mean (SEM). Bar in a=15 μm in FIGS. 21A-21F.

FIGS. 22A-22E. ESHU augments neuroprotection by bone marrow stromal cell transplants in the contused spinal cord. Damage and loss of nervous tissue was observed at four weeks after a bone marrow stromal cell (BMSC) transplant in ESHU (A) or PBS (B) or ESHU (C) or PBS (D) alone into the contused spinal cord. (E) Bar graph showing that spared tissue volume was larger with the transplant in ESHU compared with all other groups. Error bars in bar graph display standard error of the mean (SEM) and asterisks indicate $p<0.05$. Bar in a=60 μm in FIGS. 22A-22D.

SEQUENCE LISTING

Figure 1:
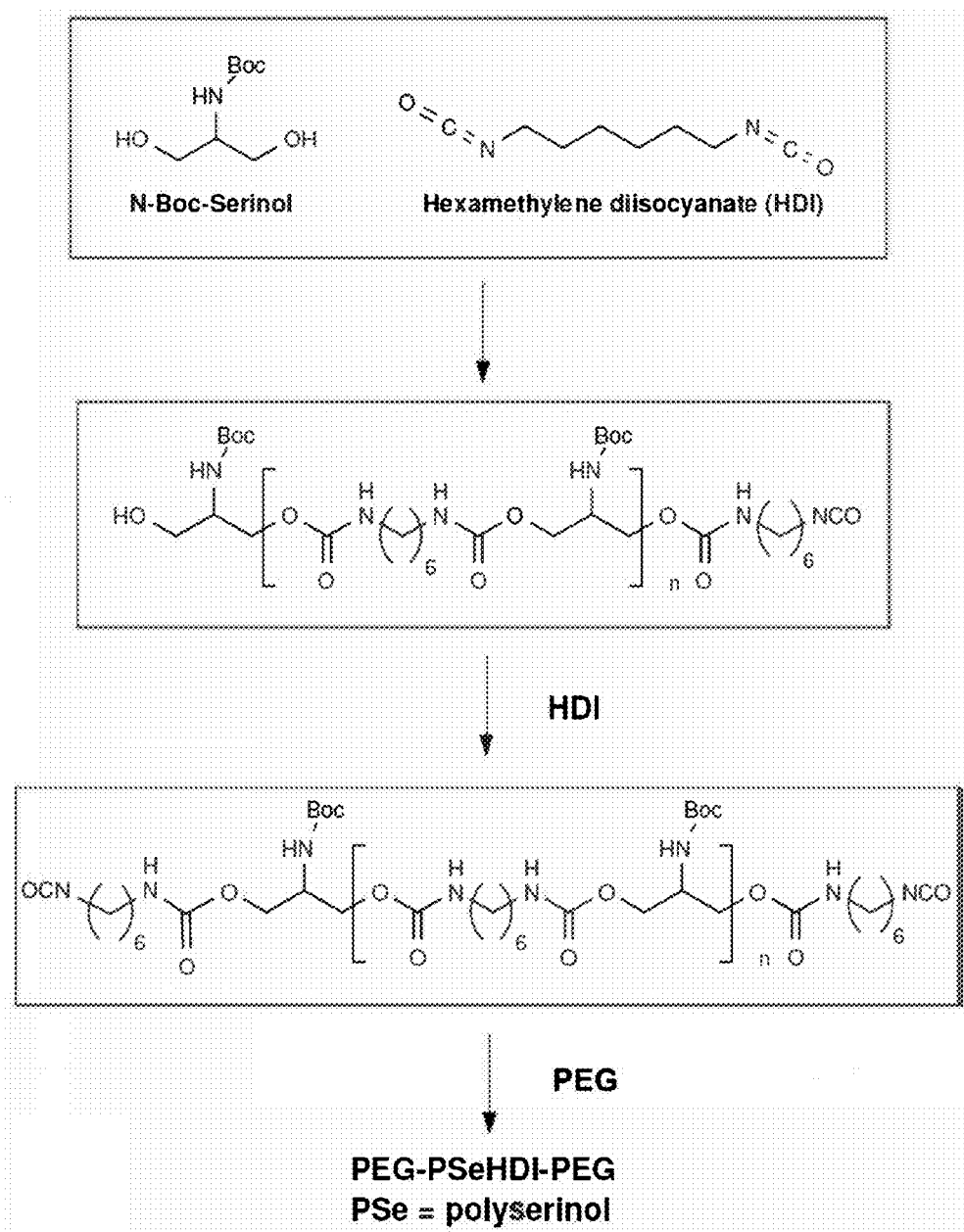
FIGS. 1 and 2. The synthesis of PEG-polyurethane (PU)-PEG and PEG-poly(ester urethane) (PEU)-PEG, respectively.

The Sequence Listing is submitted as an ASCII text file [8123-8128-02_Sequence_Listing.txt, Aug. 12, 2014, 3.54 KB], which is incorporated by reference herein.

DETAILED DESCRIPTION OF SEVERAL EMBODIMENTS

Methods are disclosed herein for increasing the number of cells, either in vitro or in vivo. The number of cells can be increased by increasing survival of the cells. The methods include administering to a subject an effective amount of cells, such as bone marrow-derived stromal cells, stem cells, Schwann cells, within a therapeutically effective amount of a reverse thermal gel composition, poly(ethylene glycol)-poly (serinol hexamethylene urethane) which is a gel at about 25° C. to ° C. 40° C., such as about 35° C. to about 40° C., and a liquid solution at a lower temperature. The reverse thermal gel compositing includes a triblock copolymer, or pharmaceutically acceptable salt thereof, having the structure B-A-B in which A is one of a polyurethane or poly(ester urethane) group that comprises one or more pendant active groups, protected active groups or active agents and B is a hydrophilic block, wherein the composition is a gel at about 35° C. to about 40° C., such as at about 37° C. and a liquid solution at a lower temperature. In specific non-limiting examples, the reverse thermal gel composition comprises poly(ethylene glycol)-poly(serinol hexamethylene urethane)).

In additional embodiments, methods are disclosed for treating a subject with a spinal cord injury or a neurodegenerative disorder. The methods include administering to a subject cells, such as bone marrow-derived stromal cells, stem cells, Schwann cells, within a therapeutically effective amount of a reverse thermal gel composition, poly(ethylene glycol)-poly(serinol hexamethylene urethane) which is a gel at about 35° C. to about 40° C. and a liquid solution at a lower temperature. In specific non-limiting examples, the reverse thermal gel composition comprises poly(ethylene glycol)-poly(serinol hexamethylene urethane). Without being bound by theory, the use of the reverse thermal gel composition can decrease the presence of reactive oxygen species and as a result increase stem cell survival.

TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Agent: Any polypeptide, compound, small molecule, organic compound, salt, polynucleotide, or other molecule of interest.

Allogeneic: Deriving from, originating in, or being members of the same species, but not being from the same individual. An "allogeneic transplant" refers to transfer of cells or organs from a donor to a recipient, where the recipient is the same species as the donor, but the recipient and the donor are not the same individual.

Alter: A change in an effective amount of a substance of interest, such as a polynucleotide or polypeptide. The amount of the substance can be changed by a difference in the amount of the substance produced, by a difference in the amount of the substance that has a desired function, or by a difference in the activation of the substance. The change can be an increase or a decrease. The alteration can be in vivo or in vitro. In several embodiments, altering an effective amount of a polypeptide or polynucleotide is at least about a 50%, 60%, 70%, 80%, 90%, 95%, 96%, 97%, 98%, 99%, or 100% increase or decrease in the effective amount (level) of a substance, the number, proliferation and/or survival of a cells. In another embodiment, an alteration affects a physiological property of a cell, such as the differentiation, proliferation, or senescence of the cell.

Animal: Living multi-cellular vertebrate organisms, a category that includes, for example, mammals and birds. The term mammal includes both human and non-human mammals. Similarly, the term "subject" includes both human and veterinary subjects.

Autologous: Deriving from or originating in the same subject or patient. An "autologous transplant" refers to collection and retransplant of a subject's own cells or organs.

Axonal growth or axonal regeneration: The ability of an axon to grow and to the ability of an axon to sprout. An axon sprout is defined as a new process that extends from an existing or growing axon. (See, e.g., Ma et al., *Nat. Neurosci.* 2:24-30 (1999)).

cDNA (complementary DNA): A piece of DNA lacking internal, non-coding segments (introns) and regulatory sequences that determine transcription. cDNA is synthesized in the laboratory by reverse transcription from messenger RNA extracted from cells.

Central Nervous System (CNS): The part of the nervous system of an animal that contains a high concentration of cell bodies and synapses and is the main site of integration of nervous activity. In higher animals, the CNS generally refers to the brain and spinal cord.

Differentiation: Refers to the process whereby relatively unspecialized cells (such as embryonic stem cells or other stem cells) acquire specialized structural and/or functional features characteristic of mature cells. Similarly, "differentiate" refers to this process. Typically, during differentiation, cellular structure alters and tissue-specific proteins appear.

Effective amount or Therapeutically effective amount: The amount of agent sufficient to prevent, treat, reduce and/or ameliorate the symptoms and/or underlying causes of any of a disorder or disease, or to increase the number of cells, such as to increase the survival and/or proliferation of cells. In one embodiment, an "effective amount" is sufficient to reduce or eliminate a symptom of a disease. In another embodiment, an effective amount is an amount sufficient to overcome the disease itself. In a further example, an effective amount of an agent is an amount that produces a statistically significant increase in the number of cells in culture as compared to a control, such as a culture not treated with the agent or treated with vehicle alone.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells, but divide to form more cells.

Hematopoietic Progenitor Cell (HPC): A self renewing pluripotent cell capable of ultimately differentiating into cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers. In humans, HSCs are typically characterized as CD34+. HPCs display a range of pluripotency and surface marker expression changes with increasing differentiation. Descriptions of marker phenotypes for various hematopoietic and myeloid progenitor cells are also described in, for example, Metcalf (2007) Stem Cells 25:2390-95; U.S. Pat. Nos. 6,465,247 and 6,761,883; Akashi (2000) Nature 404: 193-97; and Manz (2002) Proc. Natl. Acad. Sd. USA 9911872-77.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Isolated: An "isolated" biological component (such as a nucleic acid, peptide, protein or cell) has been substantially separated, produced apart from, or purified away from other biological components of the organism in which the component naturally occurs, i.e., other chromosomal and extrachromosomal DNA and RNA, cells and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. Similarly, an "isolated" cell has been substantially separated, produced apart from, or purified away from other cells of the organism in which the cell naturally occurs. Isolated cells can be, for example, at least 99%, at least 98%, at least 95%, at least 90%, at least 85%, or at least 80% pure Mesenchymal Stem Cell (MSC): A pluripotent cell that can differentiate into a number of different cell types. MSCs are commonly harvested from bone marrow, but can be found in and isolated from other tissues such as adipose, liver, olfactory, and fetal tissues. MSCs express a number of cell surface markers. Human MSCs typically do not express CD34 or CD45, but can express CD105, CD73, CD44, CD90 (Thy-1), CD71, and CD106. See, e.g., Campagnoli et al. (2001) *Blood* 98:2396-2402.

Nerve: A single bundle of nerve fibers or a plurality of bundles of nerve fibers. "Nerve regeneration" refers to axonal regeneration and restoration of connectivity within neural networks after nerve injury or damage. For example, nerve regeneration can include complete axonal nerve regeneration, including vascularization and reformation of the myelin sheath. More specifically, when a nerve is severed, a gap is formed between the proximal and distal portions of the injured nerve. In order for the nerve axon to regenerate and reestablish nerve function, it must navigate and bridge the gap. Nerve regeneration involves the proximal end forming neurite growth cones that navigate the gap and enter endoneural tubes on the distal portion, re-connecting the neural network. Thus, a necessary action for nerve regeneration is sufficient neurite elongation as well as a sufficient rate of neurite elongation. In certain examples, the desirable neurite elongation is significantly greater than that achieved with nerve growth factor alone in cell cultures as described below. For instance, the neurite elongation may be at least about 200 µm, and more particularly about 200 µm to about 1000 µm, in treated cells at 168 hours. With respect to nerve regeneration in animals, a functional improvement may be observed, for example, with at least about a 15% increase in the rate of neurite elongation, more particularly at least about a 30% rate increase, relative to the rate of neurite elongation for untreated nerve injuries.

Neurological disorder: A disorder in the nervous system, including the central nervous system (CNS) and peripheral nervous system (PNS). Examples of neurological disorders include Parkinson's disease, Huntington's disease, Alzheimer's disease, severe seizure disorders including epilepsy, familial dysautonomia as well as injury or trauma to the nervous system, such as neurotoxic injury or disorders of mood and behavior such as addiction, schizophrenia and amyotrophic lateral sclerosis. Neuronal disorders also include Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or schizophrenia.

Neurodegenerative disorder: An abnormality in the nervous system of a subject, such as a mammal, in which neuronal integrity is threatened. Without being bound by theory, neuronal integrity can be threatened when neuronal cells display decreased survival or when the neurons can no longer propagate a signal. Specific, non-limiting examples of a neurodegenerative disorder are Alzheimer's disease, Pantothenate kinase associated neurodegeneration, Parkinson's disease, Huntington's disease (Dexter et al., *Brain* 114:1953-1975, 1991), HIV encephalopathy (Miszkziel et al., *Magnetic Res. Imag.* 15:1113-1119, 1997), and amyotrophic lateral sclerosis.

Alzheimer's disease manifests itself as pre-senile dementia. The disease is characterized by confusion, memory failure, disorientation, restlessness, speech disturbances, and hallucination in mammals (*Medical, Nursing, and Allied Health Dictionary*, 4th Ed., 1994, Editors: Anderson, Anderson, Glanze, St. Louis, Mosby). Alzheimer's disease is characterized by a progressive loss of neurons, formation of fibrillary tangles within neurons and numerous plaques in affected brain regions. It is believed that the key pathogenic event in Alzheimer's disease is the excessive formation and/or accumulation of fibrillar β-amyloid peptides, which are also called αβ.

Parkinson's disease is a slowly progressive, degenerative, neurologic disorder characterized by resting tremor, loss of postural reflexes, and muscle rigidity and weakness (*Medical, Nursing, and Allied Health Dictionary*, 4th Ed., 1994, Editors: Anderson, Anderson, Glanze, St. Louis, Mosby).

Amyotrophic lateral sclerosis is a degenerative disease of the motor neurons characterized by weakness and atrophy of the muscles of the hands, forearms and legs, spreading to involve most of the body and face (*Medical, Nursing, and Allied Health Dictionary*, 4th Ed., 1994, Editors: Anderson, Anderson, Glanze, St. Louis, Mosby).

Pantothenate kinase associated neurodegeneration (PKAN, also known as Hallervorden-Spatz syndrome) is an autosomal recessive neurodegenerative disorder associated with brain iron accumulation. Clinical features include extrapyramidal dysfunction, onset in childhood, and a relentlessly progressive course (Dooling et al., *Arch. Neurol.* 30:70-83, 1974). PKAN is a clinically heterogeneous group of disorders that includes classical disease with onset in the first two decades, dystonia, high globus pallidus iron with a characteristic radiographic appearance (Angelini et al., *J. Neurol.* 239:417-425, 1992), and often either pigmentary retinopathy or optic atrophy (Dooling et al., *Arch. Neurol.* 30:70-83, 1974; Swaiman et al., *Arch. Neurol* 48:1285-1293, 1991).

A "neurodegenerative related disorder" is a disorder such as speech disorders that are associated with a neurodegenerative disorder. Specific non-limiting examples of a neurodegenerative related disorders include, but are not limited to, palilalia, tachylalia, echolalia, gait disturbance, preservative movements, bradykinesia, spasticity, rigidity, retinopathy, optic atrophy, dysarthria, and dementia.

Peripheral Nervous System (PNS): The part of an animal's nervous system other than the Central Nervous System. Generally, the PNS is located in the peripheral parts of the body and includes cranial nerves, spinal nerves and their branches, and the autonomic nervous system.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Pharmaceutical agent: A chemical compound, small molecule, or other composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polymer: A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone or are removed in the polymerization process. A polymer is said to comprise a specific type of linkage if that linkage is present in the polymer.

Self-renewal: The ability of a cell to divide and generate at least one daughter cell with the self-renewing characteristics of the parent cell. Mesenchymal stem cells, like other pluripotent stem cells, are self-renewing. The second daughter cell may commit to a particular differentiation pathway. For example, a self-renewing hematopoietic stem cell can divide and form one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype. "Non-self renewing" refers to cells that undergo cell division to produce daughter cells, neither of which have the differentiation potential of the parent cell type, but instead generates differentiated daughter cells.

Senescence: The inability of a cell to divide further. A senescent cell is still viable, but does not divide.

Stem cell: A cell that can generate a fully differentiated functional cell of a more than one given cell type. The role of stem cells in vivo is to replace cells that are destroyed during the normal life of an animal. Generally, stem cells can divide without limit and are totipotent or pluripotent. After division, the stem cell may remain as a stem cell, become a precursor cell, or proceed to terminal differentiation. A nervous system (NS) stem cell is, for example, a cell of the central nervous system that can self-renew and can generate astrocytes, neurons and oligodendrocytes.

A "somatic precursor cell" is a cell that can generate a fully differentiated functional cell of at least one given cell type from the body of an animal, such as a human. Generally, precursor cells can divide and are pluripotent. After division, a precursor cell can remain a precursor cell, or may proceed to terminal differentiation.

The term "pluripotent" or "pluripotency" refers to stem cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

Stromal cell: Connective tissue cells of any organ, for example in the uterine mucosa (endometrium), prostate, bone marrow, and the ovary. They are cells that support the function of the parenchymal cells of that organ. Fibroblasts, immune cells, pericytes, and inflammatory cells are the most common types of stromal cells.

Subject: Any mammal, such as humans, non-human primates, pigs, sheep, cows, rodents and the like, which is to be the recipient of the particular treatment. In one embodiment, a subject is a human subject or a murine subject.

Survival (of a Cell): The length of time a given cell is alive. An increase in survival following treatment indicates that the cell lives for a longer length of time as compared to a control, such as the cell in the absence of treatment.

Therapeutic agent: Used in a generic sense, it includes treating agents, prophylactic agents, and replacement agents.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed., *Gene Therapeutics*, Birkhauser, Boston, USA (1994)). In the case of infection by retroviruses, the infecting retrovirus particles are absorbed by the target cells, resulting in reverse transcription of the retroviral RNA genome and integration of the resulting provirus into the cellular DNA. Methods for the introduction of genes into the pancreatic endocrine cells are known (e.g. see U.S. Pat. No. 6,110,743, herein incorporated by reference). These methods can be used to transduce a pancreatic endocrine cell produced by the methods described herein, or an artificial islet produced by the methods described herein.

Genetic modification of the target cell is one indicia of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene supplied by a vector.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Reverse Thermal Gels

The disclosure of U.S. Published Patent Application No. 2013/0129663 is incorporated herein by reference. As used in this publication and herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

The term "alkyl" refers to both branched and straight-chain saturated aliphatic hydrocarbon groups. These groups can have a stated number of carbon atoms, expressed as $C_{x-y}$, where x and y typically are integers. For example, $C_{5-10}$, includes $C_5$, $C_6$, $C_7$, $C_8$, $C_9$, and $C_{10}$. Alkyl groups include, without limitation: methyl, ethyl, propyl, isopropyl, n-, s- and t-butyl, n- and s-pentyl, hexyl, heptyl, octyl, etc. Alkenes comprise one or more double bonds and alkynes comprise one or more triple bonds. These groups include groups that have two or more points of attachment (e.g., alkylene). Cycloalkyl groups are saturated ring groups, such as cyclopropyl, cyclobutyl, or cyclopentyl. Aromatic groups include one or more benzene rings. As used herein, "halo" or "halogen" refers to fluoro, chloro, bromo, and iodo. An amine is a group having the structure —N(R1)(R2). Where R1 and R2 are H, the group is amino.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone or are removed in the polymerization process. A polymer is said to comprise a specific type of linkage if that linkage is present in the polymer.

The polymers disclosed in are bioerodible or biodegradable. By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months. Non-limiting examples of such chemical reactions include acid/base reactions, hydrolysis reactions, and enzymatic cleavage. The polymers described herein contain labile ester linkages. The polymer or polymers may be selected so that it degrades over a time period. Non-limiting examples of useful in situ degradation rates include between 12 hours and 5 years, and increments of hours, days, weeks, months or years therebetween. For example, in the context of an drug product to be injected via the intravitreal route, the polymer may preferably degrade over 1, 2, 3, 4, 5, 6, 7, 8, 9, 10, 11, or 12 months, or longer.

Provided is a reverse thermal gel composition comprising a triblock copolymer having the structure B-A-B in which A is one of a polyurethane or poly(ester urethane) group that comprises one or more pendant active groups, blocked active groups or active agents and B is a hydrophilic block that can be PEG of various sizes, hyaluronan of various sizes, poly (vinyl alcohol) or oligo(vinyl alcohol), polycarbohydrage, etc. Examples of poly(ethylene glycol) average molecular weights include 350, 550, 750, 1000, and 1900 Da. The composition is in solution at a lower temperature, e.g., at room temperature and transitions to a gel as the temperature is raised, to form a complete gel at a higher temperature, e.g., physiological (body) temperature (e.g., 35° C.-40° C.). The transition temperature also may be referred to as the Lower Critical Solution Temperature, or LCST) is preferably 30° C. or less or 25° C.-30° C. As an example, the transition point is above room temperature (RT, for example 25° C.) and physiological temperature (typically 37° C. but there can be individual differences). As a further example, the composition begins transformation as the temperature rises from 25° C. and forms a gel around 33-35° C. and still remains gel at 37° C. In another example, the composition gels between 25° C. to 40° C. and is a liquid solution at temperatures below 25° C. (e.g., 24° C., 23° C., etc.). The triblock copolymer may be converted to a pharmaceutically acceptable salt. In one embodiment, A is a copolymer of a diol (a hydrocarbon comprising aliphatic or aromatic groups and which may be saturated or unsaturated) and a diisocyanate. The diol may be amino-substituted or N-substituted serinol, such as N-boc serinol, in which the N is substituted with one of a hydrogen, a protective group (a removable group that prevents the amine or other desirable moiety from reacting during synthesis of the triblock copolymer), or an active agent. In some embodiments, the diol is a polymer or an oligomer with terminal primary alcohol functional group ends. In another embodiment, the N of the N-substituted serinol is —NHR in which R is a protective group, such as carbobenzyloxy; p-methoxybenzyl carbonyl; tert-butyloxycarbonyl; 9-fluorenylmethyloxycarbonyl; benzyl; p-methoxybenzyl; 3,4-dimethoxybenzyl; p-methoxyphenyl; tosyl; nosyl (4-nitrobenzenesulfonyl) and 2-nitrobenzenesulfonyl.

In another embodiment, the diol comprises one or more ester groups, as when it is a reaction product of a cyclic anhydride and a diol comprising one or more pendant active groups, blocked active groups or active agents. For example, the diol in one particular embodiment is the reaction product of succinic anhydride and an N-substituted serinol in which the N is substituted with one of a hydrogen, a protective group, such as carbobenzyloxy; p-methoxybenzyl carbonyl; tert-butyloxycarbonyl; 9-fluorenylmethyloxycarbonyl; benzyl; p-methoxybenzyl; 3,4-dimethoxybenzyl; p-methoxyphenyl; tosyl; nosyl (4-nitrobenzenesulfonyl) and 2-nitrobenzenesulfonyl, or an active agent. In one embodiment, the diol comprises a pendant amino group or an amine. One example of a diisocyanate is hexamethylene diisocyanate (1,6-diisocyanatohexane).

According to one embodiment, the composition comprises a copolymer comprising the structure:

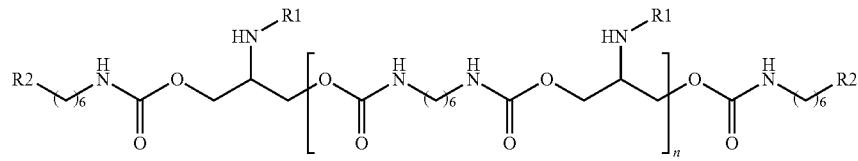

in which R1 is H or a protective group, R2 is isocyanate or —NC(O)-PEG and n is greater than 5, for example and without limitation, 8-30, 8-25 or 18-30.

According to another embodiment, the composition comprises a copolymer comprising the structure:

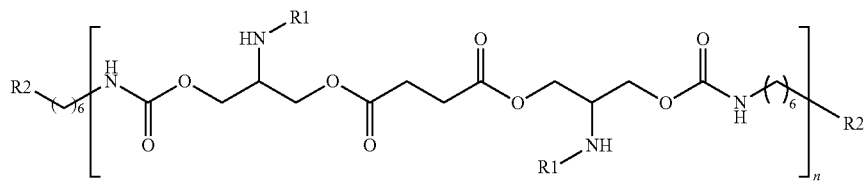

in which R1 is H or a protective group or an active agent, R2 is isocyanate or —NC(O)-PEG and n is greater than 5, for example and without limitation, 8-30, 8-25 or 18-30.

In one embodiment, the triblock copolymer has an average molecular weight of between about 3,000-50,000 Da (Daltons), for instance between 5,000 and 10,000 Da, excluding, when present, the molecular weight of the active agent. The composition may comprise an active agent complexed (non-covalently bound) to a triblock copolymer as described above.

Also provided is a method of delivering an active agent to a patient, comprising delivering to the patient a reverse thermal gel composition comprising an active agent and a triblock copolymer having the structure B-A-B in which A is one of a polyurethane or poly(ester urethane) group that comprises one or more pendant active groups, blocked active groups or active agents and B is a poly(ethylene glycol) and which is a gel at 37° C. and a liquid at a temperature below 30° C. The composition may be any composition described above, for example a composition comprising a triblock copolymer chosen from one of:

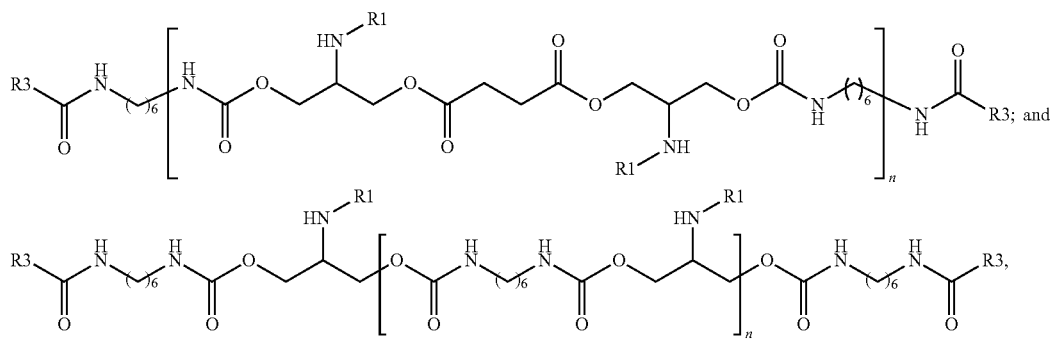

in which R1 is H and R3 is PEG, and which is complexed with an another agent, such as bevacizumab.

In one specific non-liming example, the reverse thermal gel composition comprises poly(ethylene glycol)-poly(serinol hexamethylene urethane).

The triblock copolymer can be produced as disclosed in U.S. Published Patent Application No. 2013/0129663, which is incorporated herein by reference. The method can include reacting a diol with a diisocyanate to produce a diol product; and PEGylating the diol product. In one embodiment, the idol is synthesized by reacting a diol precursor with a cyclic anhydride. An example of a diol precursor is N-serinol in which the N is substituted with a protective group, such as Boc such that the diol precursor is N-boc-serinol. In another embodiment, the cyclic anhydride is succinic anhydride. Any embodiment of these methods may further comprise complexing the triblock copolymer with an active agent. In one embodiment, the diol precursor is N-serinol, in which the N is substituted with a protective group, for instance N-boc serinol. In yet another embodiment, the diisocyanate is hexamethylene diisocyanate.

The polymer compositions may be modified to include biologically active groups or active agents either covalently bound (attached) to the polymer structure or bound to the structure non-covalently. Active agents can be admixed with the polymer composition, absorbed or adsorbed into the composition. Active agents that may be incorporated into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethisone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, bevacizumab, neovastat; (3) antiproliferatives such as sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (.+−.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate.

Active agents that may be bound to the polymer composition include peptides (e.g., ECM epitopes) for functionalizing the gel with a biologically functional group. Useful peptides include or consist of the following amino acid sequences: IKLLI (SEQ ID NO: 1)(anti-apoptotic), REDV (SEQ ID NO: 2), LDV, RGDSP (SEQ ID NO: 3), RGDV (SEQ ID NO: 4), LRGDN (SEQ ID NO: 5), RGDT (SEQ ID NO: 6), YIGSR (SEQ ID NO: 7), TTSWSQ (SEQ ID NO: 8), AEIDGIEL (SEQ ID NO: 9), WYRGRL (SEQ ID NO: 10), SIKVAVS (SEQ ID NO: 11), PDSGR (SEQ ID NO: 12), RNIAEIIKDI (SEQ ID NO: 13), DGEA (SEQ ID NO: 14), VTXG (SEQ ID NO: 15), PRRARV (SEQ ID NO: 16), YEKPGSPPREV-VPRPRPGV (SEQ ID NO: 17), RPSLAKKQRFRHRN-RKGYRSQRGHSRGR (SEQ ID NO: 18), RIQNLLKITNL-RIKFVK (SEQ ID NO: 19), RGD, IKVAV (SEQ ID NO: 20) and IKVAVS (SEQ ID NO: 21). In one example, these oligopeptides are linked via their amine groups to the polymeric structures described herein. In another embodiment, biomolecules are attached or bound to the polymer composition which aid in evasion of an immune response. Non-limiting examples of such peptides are: betaine, derivatives of betaine, and other zwitterionic groups including certain amino acids and their derivatives.

The active agent or any compound or composition may be bound to the polymer in any useful manner, for instance: covalently (including by coordination and by use of a suitable linkers and linking methods as are broadly known and are broadly available in the art, for example linkers and methods of use of linkers are commercially available from Thermo Fisher Scientific, Pierce Protein Research Products, Rockford, Ill., see also Thermo Scientific Pierce Crosslinking Technical Handbook, 2009 Thermo Fisher Scientific Inc.), by affinity or charge (that is, non-covalently), or by intermixing with the polymer when the composition is in solution phase. Binding of the active agent or any compound or composition by affinity or charge, e.g., by polar, hydrogen bonding, charge (ionic/electrostatic), or van der Waals interactions, may be preferred in many instances because the compound is not free to diffuse prior to or after gelation, as in the case of the active agent being intermixed with the polymer in the composition, or is not covalently modified, which can hamper efficacy of the active agent.

The composition comprising the reverse thermal gel and stem cell can be delivered in any useful fashion. An anti-inflammatory agent may be administered in an amount effective to decrease inflammation and pain associated with a given condition. Steroidal anti-inflammatories and non-steroidal anti-inflammatories (NSAIDs) suitable for use include, without limitation: nepafenac (for example and without limitation, Nevenac 0.1%, nepafenac ophthalmic suspension, Alcon Laboratories, Inc.), ketorolac tromethamine (for example and without limitation, Acular LS 0.4%, ketorolac tromethamine ophthalmic suspension, Allergan, Inc.), acetaminophen and bromfenac (for example and without limitation, Xibrom 0.09%, bromfenac ophthalmic suspension, Ista Pharmaceuticals). Thus, also provided herein is a composition comprising the described block copolymer and a pharmaceutically acceptable anti-inflammatory suitable for use. These anti-inflammatory compounds often exhibit analgesic effects. In any case, according to the methods described herein, the binding reagent and the anti-inflammatory may be contained in the same composition, but also may be administered separately in a manner effective to treat the infection.

An antibiotic also may be administered along with the block copolymer and, optionally, the anti-inflammatory agent may also be co-administered with the antibiotic, all in an amount effective to treat and/or prevent infection and/or its symptoms. Non-limiting examples of suitable antibiotics include: ciprofloxacin, norfloxacin, afloxacin, levofloxacin, gentamicin, tobramycin, neomycin, erythromycin, trimethoprim sulphate, and polymixin B. Antiviral compounds also may be administered in this manner, such as ganciclovir or fomivirsen.

In any case, as used herein, a therapeutically effective amount of an active agent used for prevention or treatment of a condition, such as a neurodegenerative disorder, or to increase cell survival. The amount and dosage regimen effective to prevent or reduce the duration and/or severity of the condition.

Non-limiting examples of growth factors suitable for use include: non-mitogenic human acidic fibroblast growth factor (nm-haFGF), neurotrophin nerve growth factor (NGF), epidermal growth factors (EGF), brain-derived neurotrophic factor (BDNF), glial cell line-derived neurotrophic factor (GDNF), neurotrophin-3 and eye-derived growth factor(s) (EDGF).

In one embodiment, a combined dosage form is provided comprising two or more of an anti-inflammatory agent, an antibiotic agent and a growth factor. For example, either an antibiotic or antiviral agent may be co-administered.

In any use for the prevention and/or treatment of any condition in a patient, a person of ordinary skill in the pharmaceutical and medical arts will appreciate that it will be a matter of simple design choice and optimization to identify a suitable dosage regimen for treatment of any given condition using the delivery systems/compositions described herein. As such, the composition may comprise a carrier, such as an opthamologically-acceptable carrier, which comprises acceptable excipients, such as, without limitation, one or more suitable: vehicle(s), solvent(s), diluent(s), pH modifier(s), buffer(s), salt(s), colorant(s), rheology modifier(s), lubricant(s), antifoaming agent(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water, as are broadly known in the pharmaceutical arts.

The compositions can be used as cell growth scaffolds. Cells may be microintegrated within a cell growth matrix using a variety of methods. In likely the simplest embodiment to implement, the cells are mixed with the copolymer when it is a miscible liquid, below the gelation temperature. The following are examples of methods used to incorporate cells, such as, but not limited to, mesenchymal stem cells and/or bone marrow stem cells, into traditional cell scaffolds that are gelled or solid at the time of cell incorporation. They may be useful in case where a cell type would need to be preconditioned to the matrix prior to implantation. In the context of the present disclosure, the gel may be warmed until it gels and then cells are incorporated, for example, as follows. In each case, the gel would need to be kept above the gelation temperature throughout. However, reduction of the temperature until the gel/cell mixture is a miscible liquid may be desirable for the purpose of either facilitating delivery to a patient through a needle or catheter, or for isolating cells, in that the solution can be centrifuged to pellet the cells.

In one example, a gel is submersed in an appropriate growth medium for the cells to be incorporated, and then directly exposed to the cells. The cells are allowed to proliferate on the surface and interstices of the matrix. The matrix is then removed from the growth medium, washed if necessary, and implanted. Cells of interest also can be dissolved into an appropriate solution (e.g., a growth medium or buffer) and then sprayed onto a growth matrix. This method is particularly suitable when a highly cellularized tissue engineered construct is desired. In one embodiment, pressure spraying (i.e., spraying cells from a nozzle under pressure) is used to deposit the cells. In another, the cells are electrosprayed onto the non-woven mesh during electrodeposition. Electrospraying involves subjecting a cell-containing solution with an appropriate viscosity and concentration to an electric field sufficient to produce a spray of small charged droplets of solution that contain cells.

Many cell types require a support cell population or matrix in order to, for example, survive, grow, propagate or differentiate. As indicated above, cells can be mixed with the composition at a temperature below the gelation temperature for the composition. Next, the temperature of the composition is raised to produce a gel containing the cells. The cells are grown at a temperature at which the composition is gelled. Lastly, the cells can be removed from the gel by first lowering the temperature of the composition to below the gelation temperature to "melt" the gel, and then the cells are washed, e.g., with medium, saline or PBS (Phosphate-Buffered Saline) to remove the polymer composition. By this method specific shapes of tissue may be generated, for instance by growing the cells in a mold, and letting the cells grow/differentiate until cell-cell interaction is achieved. Once the cells or tissue is grown, the cells or tissue can then be washed free of any remaining polymer.

Many cell types may be incorporated on or into the gel including stem cells, (such as mesenchymal stem cells, neural stem cells; progenitor (precursor) cells), bone-marrow derived stromal cells, Schwann cells, and genetically modified forms of these cells. In certain embodiments, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF or FGF-2), acidic fibroblast growth factor (aFGF), nerve growth factor (NGF), vascular endothelial growth factor (VEGF), hepatocyte growth factor (HGF), insulin-like growth factors (IGF), transforming growth factor-beta pleiotrophin protein, midkine protein.

In one embodiment of the methods described herein, the composition, with or without cells, growth factors, active agents, etc. is injected or deposited locally. The composition remains at a temperature at which it is a gel. The composition with or without cells, growth factors, active agents, etc., can be injected or otherwise administered at any point in or on a subject. For instance a catheter, cannula, trochar, syringe, etc. can be used to deliver the composition to a desired location. In one embodiment, a method of growing nerve cells, such as a method of repairing a nerve, or treating a degenerative disorder, is provided. For example, the composition can be implanted at a site of a spinal cord wound (see below for an example) and the nerve tissue is regenerated.

Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

As described above, the compositions are useful for drug delivery, especially were systemic treatment is not necessary or dangerous. One or more therapeutic agents may be included in the compositions and the composition is delivered to a site in a patient, where the composition gels. Delivery of the composition is limited by the rate of degradation of the polymeric component of the composition.

Methods for Increasing the Survival of Cell Transplants

Methods are disclosed herein for increasing the survival of transplanted cells, such as bone marrow-derived stromal cells (BMSCs), stem cells, and Schwann cells, and others.

The cell can be from any organ. In some embodiments, the cell can be a connective tissue cell of any organ, for example in the uterine mucosa (endometrium), prostate, bone marrow, and the ovary. Fibroblasts, immune cells, pericytes, and inflammatory cells are stromal cells; these cells can be utilized. In some embodiments, the cell is a bone marrow stromal cell. The cell can be a stem cell or a progenitor cells, such as, but not limited to, a hematopoietic progenitor cell. The cell can be an embryonic stem cell or an induced pluripotent stem cell.

In some embodiments, the cells can include a heterologous nucleic acid. For example, the cells can be transfected with a vector encoding a protein or an antisense construct. Standard recombinant methods are used for cloning, DNA and RNA isolation, amplification and purification. Generally, enzymatic reactions involving DNA ligase, DNA polymerase, restriction endonucleases and the like are performed according to the manufacturer's specifications. Basic texts disclosing the general methods of use in this invention include Sambrook and Russell eds. (2001) *Molecular Cloning: A Laboratory Manual*, 3rd edition; the series Ausubel et al. eds. (2007 with updated through 2010) *Current Protocols in Molecular Biology*, among others known in the art.

Cells of use in the methods disclosed herein can be allogeneic or autologous. Thus, in some embodiments, the cells used in the method disclosed herein are isolated from the same subject wherein they are utilized with the reverse thermal gel. The cells can be primate cells, such as human cells, or veterinary cells, such as cells from a domesticated animal. In some embodiments, the cells are cultured and allowed to divide. The cells can be primary cells or cells from a cell line.

A bone marrow stem cell is an adult, mesoderm-derived cell that is capable of generating cells of mesenchymal lineages, typically of two or more mesenchymal lineages, e.g., osteocytic (bone), chondrocytic (cartilage), myocytic (muscle), tendonocytic (tendon), fibroblastic (connective tissue), adipocytic (fat) and stromogenic (marrow stroma) lineage. Mesencymal stem cells (MSC) may be isolated from, e.g., bone marrow, blood, umbilical cord, placenta, foetal yolk sac, skin (dermis), specifically fetal and adolescent skin, periosteum and adipose tissue. Human MSC, their isolation, in vitro expansion, and differentiation, have been described in, e.g., U.S. Pat. No. 5,486,359; U.S. Pat. No. 5,811,094; U.S. Pat. No. 5,736,396; U.S. Pat. No. 5,837,539; and U.S. Pat. No. 5,827,740. MSCs can be obtained from a number of tissues, such as adipose tissue, olfactory epithelia, bone marrow, liver, amniotic fluid, etc. MSC can be isolated from bone marrow (or other sources) by selecting those (mononuclear) cells which can adhere to a substrate surface, e.g., plastic surface. A number of commercially available products are available for isolation from primary tissues, such as ROSET-TESEP® Human MSC Enrichment Cocktail and EASYSEP®MSC Enrichment Kit. Isolation can be based on MSC cell surface markers, but also account for morphology and size of MSCs. Methods for isolating MSCs are further described in You et al. (2009) *Int'l J Gynecol. Obstetrics* 103:149-52 and Alhadlaq & Mao (2004) *Stem Cells and Development* 13:436-448. Suitable culture conditions for MSCs are described herein, and can include standard tissue culture conditions. For example, the MSCs can be cultured in a buffered media that includes amino acids, nutrients, growth factors, etc, as will be understood in the art. In some aspects, the culture includes feeder cells (e.g., fibroblasts), while in others, the culture is devoid of feeder cells. Cell culture conditions are described in more detail, e.g., in Picot, *Human Cell Culture Protocols (Methods in Molecular Medicine)* 2010 ed. and Davis, *Basic Cell Culture* 2002 ed.

Mesenchymal Stem Cells (MSCs) present several characteristics making them an attractive cell population for cell-therapy. For example, MSCs are "immune privileged." Without being bound by theory, MSCs are less likely to cause Graft Versus Host Disease or require immunosuppressants for cell therapy regimens. MSCs are readily available from a variety of adult tissues (e.g., olfactory, bone, adipose, bone marrow) allowing for autologous transplantation without the need for highly invasive techniques. Indeed, MSC cultures can be established by methods known in the art, and the high proliferation rate allows for rapid expansion of initial cultures. Moreover, MSCs have been shown to be an adequate cell source for differentiation into a variety of different cell types including e.g., osteocytes, chondrocytes, smooth muscle, cardiomyocytes and adipocytes.

Bone marrow stem cells are present in or (partly) isolated from a sample of bone marrow. A sample of bone marrow may be obtained, e.g., from iliac crest, femora, tibiae, spine, rib or other medullar spaces of a subject. Bone marrow stem cells encompass any and all subtypes thereof, such as without limitation, "rapidly self-renewing cells" RS-1 or RS-2 as described in Colter et al. 2000 (PNAS 97(7): 3213-8); "side population" (SP) cells as described by Goodell et al. 1997 (Nat Med 3(12): 1337-45); osteogenic precursor (OP) cells which are initially identified by their low density (e.g., upon density gradient centrifugation), non-adherent nature and low-level of expression of osteogenic markers (as described by Long et al. 1995. J Clin Invest. 95(2): 881-7; U.S. Pat. No. 5,972,703); primitive precursor cells which can generate cells of both the haematopoietic and non-haematopoietic lineages as described by Krause et al. 2001 (Cell 105: 369-377) and Dominici et al. 2004. (PNAS 101(32): 11761-6); and others. In some embodiments, the bone marrow stem cells can include a heterologous nucleic acid (see above).

Methods are disclosed herein for increasing neurite outgrowth and/or promoting nerve regeneration in a subject. In one example, the subject has a degenerative disorder of the nervous system. In another embodiment, the subject has a partially or completely transected nerve. In additional examples, the subject has a partial transection of the spinal cord or a peripheral nerve. In further examples, the subject has a complete transection of the spinal cord or a peripheral nerve.

The subject can be any subject of interest. The method is useful in the treatment of animals (including mammals such as humans) having a neurological condition associated with neuronal dysfunction caused by disease or injury to neurons in either the central or peripheral nervous systems. Compositions, such as the reverse thermal gel and cells, are administered in a therapeutically effective neurotrophic amount, such as an amount sufficient to promote neurite outgrowth from neurons. The method can also be used in association with procedures such as a surgical nerve graft, or other implantation of neurological tissue, to promote healing of the graft or implant, and promote incorporation of the graft or implant into adjacent tissue. In some embodiment, the method includes delivering to a site in or on the patient a reverse thermal gel composition and cells as described herein. The composition can be delivered by a needle, cannula, catheter, trochar or any similar devices.

The compositions and methods disclosed herein may be useful whenever nerve regeneration is sought, for example following any acute or chronic nervous system injury resulting from physical transection/trauma, contusion/compression or surgical lesion, vascular pharmacologic insults including hemorrhagic or ischemic damage, or from neurodegenerative or other neurological diseases. The methods can be used in a subject with a stroke.

The methods can also be used in association with procedures such as a surgical nerve graft, or other implantation of neurological tissue, to promote healing of damaged tissue, and promote survival of the graft or implant. According to another embodiment, the compositions could be coated or otherwise incorporated into a device or biomechanical structure designed to promote nerve regeneration.

More particularly, pharmaceutical compositions cells and the reverse thermal gel composition disclosed herein, can be administered to a mammalian patient (such as, but not limited to, a human subject), in need of such treatment, to promote neuronal regeneration and functional recovery and to stimulate neurite outgrowth and thereby to treat various neuropathological states, including damage to peripheral nerves and the central nervous system caused by physical injury (e.g., spinal cord injury; trauma, sciatic or facial nerve lesion or injury; severed appendage), disease (e.g., diabetic neuropathy), cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barre syndrome, Alzheimer's disease, Parkinson's disease, and Huntington's chorea. In another embodiment, the subject has a "neurodegenerative-related disorder" such as palilalia, tachylalia, echolalia, gait disturbance, preservative movements, bradykinesia, spasticity, rigidity, retinopathy, optic atrophy, dysarthria, or dementia.

In some embodiments, the reverse thermal gel composition and cells are used for substantially complete axonal nerve regeneration, including vascularization and reformation of the myelin sheath, of a transected nerve of the peripheral nervous system in which the transection was caused by a trauma such as an accidental or intentional severing of the nerve. Such regeneration restores neural connectivity of the transected nerve.

The methods can also be used in association with procedures such as a surgical nerve graft, or other implantation of neurological tissue, to promote healing of the graft or implant, and promote incorporation of the graft or implant into adjacent tissue. According to another aspect, the compositions could be coated or otherwise incorporated into a device or biomechanical structure designed to promote nerve regeneration.

In one embodiment, a transection of a peripheral nerve or a spinal cord injury can be treated. The method can include grafting to the peripheral nerve or spinal cord an allograft (Osawa et al., *J. Neurocytol.* 19:833-849, 1990; Buttemeyer et al., *Ann. Plastic Surgery* 35:396-401, 1995) or an artificial nerve graft (Madison and Archibald, *Exp. Neurol.* 128:266-275, 1994; Wells et al., *Exp. Neurol.* 146:395-402, 1997). The transection can be a partial or a complete transection.

In a certain examples, the reverse thermal gel and cells are disposed in a nerve guidance channel which spans the distance of the damaged pathway. The channel acts both as a protective covering and a physical means for guiding growth of a neurite. Useful channels include a biocompatible membrane, which may be tubular in structure, having a dimension sufficient to span the gap in the nerve to be repaired, and having openings adapted to receive severed nerve ends. The membrane can be made of any biocompatible, nonirritating material, such as silicone or a biocompatible polymer, such as polyethylene or polyethylene vinyl acetate. The casing also may be composed of biocompatible, bioresorbable polymers, including, for example, collagen, hyaluronic acid, polylactic, polybutyric, and polyglycolic acids. In one embodiment, the outer surface of the channel is substantially impermeable.

Without being bound by theory, the reverse thermal gels disclosed herein scavenges reactive oxygen species (ROS) and as a result increases survival of the cells. Thus, methods are provided herein for increasing cell survival using the reverse thermal gels disclosed herein. The cells can be, for example, mesenchymal stem cells or bone marrow stem cells, or Schwann cells. The cells can be in vivo or in vitro. In further embodiments, the disclosed method can include measuring cell survival and/or measuring reactive oxygen species.

The disclosure is illustrated by the following non-limiting Examples.

EXAMPLES

Example 1

Design and Synthesis

This study disclosed below discloses injectable reverse thermal gelling triblock copolymers with serinol-derived polyurethane (PU) and polyester urethane (PEU) and its potential as nerve regenerative matrices. PUs are useful materials in biomedical fields since they have been proven to be biocompatible (Zdrahala, R. J.; Zdrahala, I. J. *J. Biomater. Appl.* 1999, 14, 67-90). They are easily tailored by changing hard segment chemistries and concentrations leading to the intended functions. (Tang, Y. W.; Labow, R. S.; Santerre, J. P. *Journal of Biomedical Materials Research* 2001, 57, 597-611 and Tang, Y. W.; Labow, R. S.; Santerre, J. P. *J. Biomed. Mater. Res.* 2001, 56, 516-528). The applications of PUs have been extended to catheters, compliant vascular grafts, and prosthetic valve leaflets since the first introduction as materials for breast prostheses.

Thus, the incorporation of biocompatible PUs with serinol and PEG resulting in functionalized injectable reverse thermal gelling copolymers is breakthrough in the field of tissue engineering, especially in the nerve regeneration.

Synthesis of Thermal Gelling Copolymers

Figure 2:
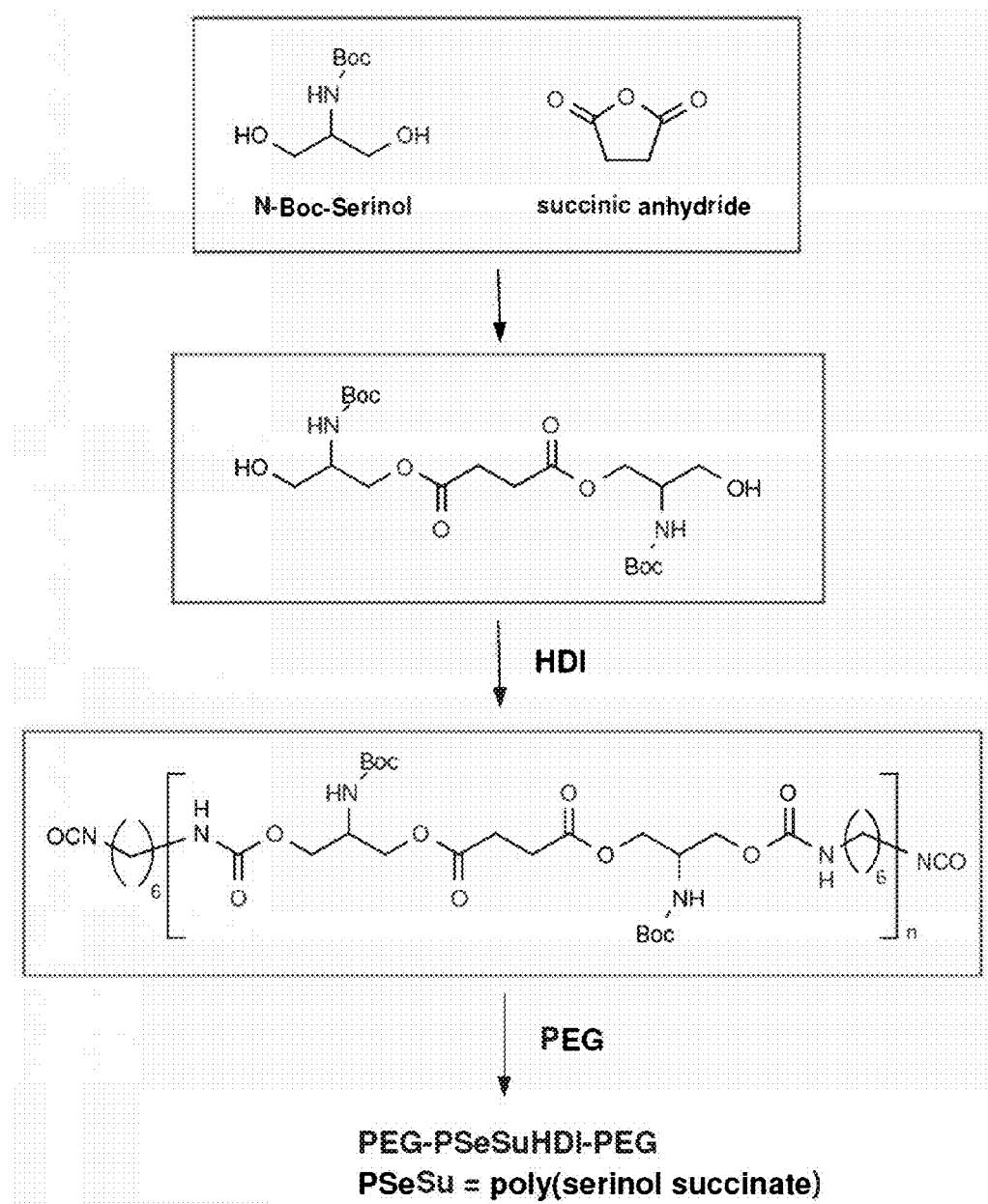

In first step, two types of thermal gelling copolymers, PEG-polyurethane (PU)-PEG and PEG-poly(ester urethane) (PEU)-PEG, were designed (See FIGS. 1 and 2). PU was synthesized using N-BOC-serinol and hexamethylene diisocyanate (HDI) at 90° C. The attachment of PEG was performed by the formation of urethane bonds with HDI. PEU was synthesized in two steps. First, the esters were synthesized using N-BOC-serinol and succinic anhydride at 90° C. Then the as-synthesized esters reacted with HDI at 90° C. to make PEU followed by PEG attachment.

Figure 3A:
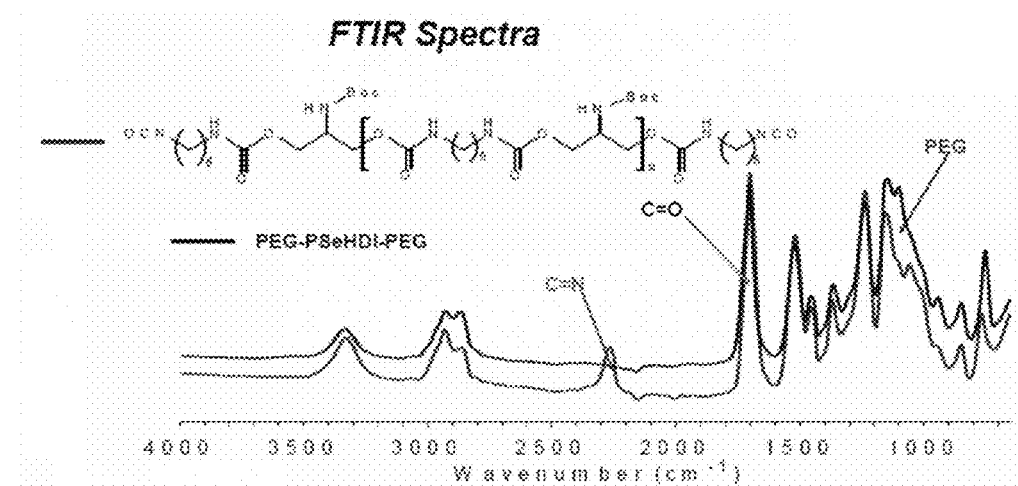
FIGS. 3A and 3B. FT-IR characterization of PEG-polyurethane (PU)-PEG and PEG-poly(ester urethane) (PEU)-PEG, respectively.
Figure 3B:
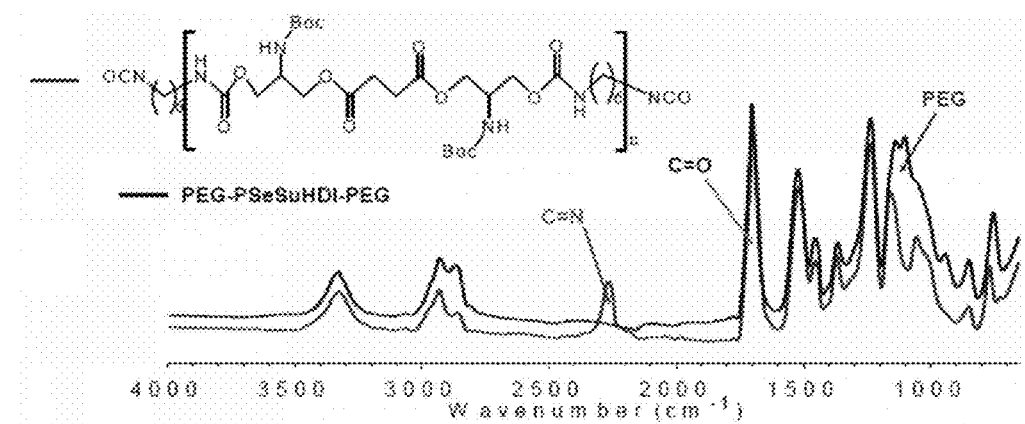

The PEG-PU-PEG was characterized by FT-IR (FIGS. 3A and 3B which showed bands of C=N by HDI and C=O by urethane bonds at 2270 and 1650-1680 $cm^{-1}$ respectively. The C=N peak disappeared after the PEG attachment whereas ether, R—O—R, signal by PEG appeared at 1000-1150 $cm^{-1}$. For the synthesis of PEG-PEU-PEG, the bands of C=N by HDI, C=O by urethane and ester bonds, and R—O—R by PEG in PEU appeared at 2270, 1600-1750, and 1000-1150 $cm^{-1}$, respectively.

Thermal Behavior of Copolymers

The phase transition from solution to gel largely depends on the balance of hydrophilic (PEG) and hydrophobic (PU, PEU) portions in copolymer structures. In addition, by modulation of the length of hydrophobic parts the gelling temperature can be adjusted. Based on these facts we developed specifically designed thermal gelling copolymers with phase transition at physiologically important temperature range of 32-37° C. The storage modus (G') of the polymer solutions in phosphate buffered saline (PBS) solution was measured by rheometer from 20° C. to 55° C.

Figures 4A, 4B:
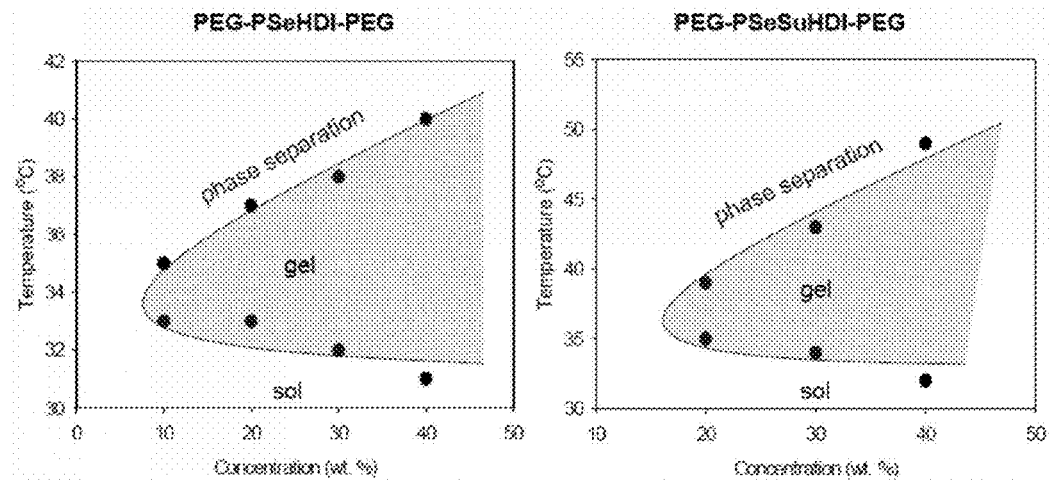
FIGS. 4A and 4B. Graphs showing thermal behavior of PEG-polyurethane (PU)-PEG and PEG-poly(ester urethane) (PEU)-PEG, respectively.

The thermal behavior showed that the aqueous polymer solution of PEG-PU-PEG prepared with 30 and 40% (wt) concentrations started phase transition from 31-32° C. and remained gel in the temperature range of 37-40° C. For the aqueous solution of PEG-PEU-PEG, they remained gel in the temperature range of 35-37° C. with all concentrations tested (FIGS. 4A and 4B). The implication of these graphs are that the compositions, with an increase in temperature will solidify, so long as the concentration of the polymer in solution is above a minimal concentration as shown in FIGS. 4A and 4B. For example, for PEG-PSeHDI-PEG, for concentrations between about 8% (wt) and 50% (wt), the composition is a solution at low temperatures, such as below about 32% (wt), and phase separation occurs at a higher temperature, such as at about 38° C. for a 30% (wt) solution of the copolymer. Thus, for typical uses in humans, a temperature range at which the composition is preferably a gel is, for example, between 32-40° C. or 32-38° C., meaning the concentration of the copolymer may be preferably between 20% (wt) to 50% (wt). For PEG-PSeSuHDI-PEG, the concentration of the copolymer may be preferably between 15% (wt) to 50% (wt).

Figure 5:
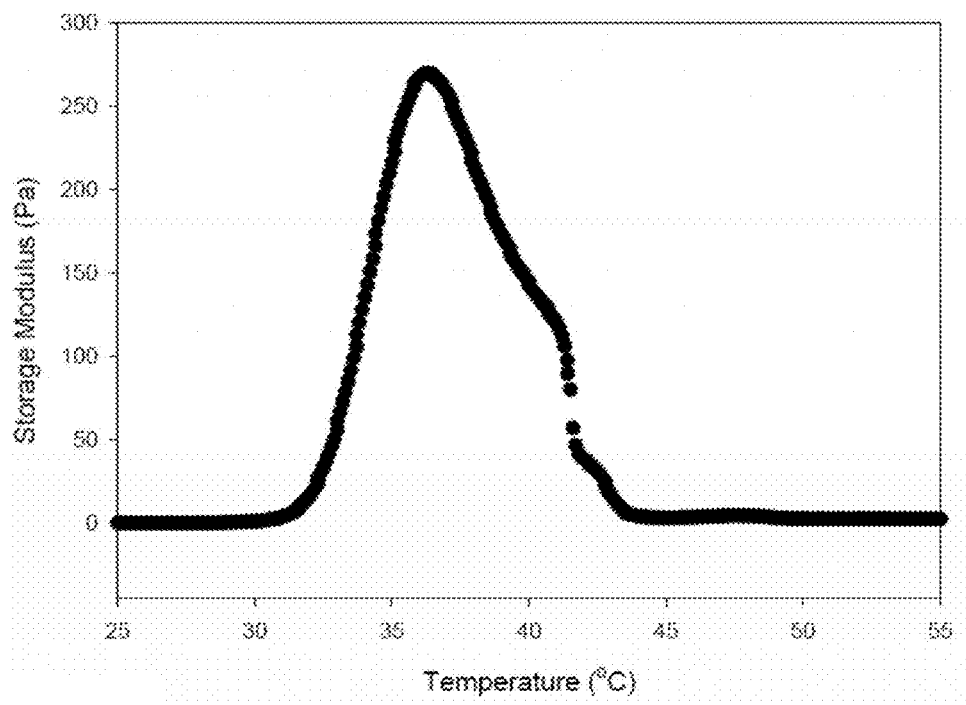
FIG. 5. Storage modulus changes of 30% (wt) PEG-PU-PEU solution.

FIG. 5 shows storage modulus changes of 30% (wt) PEG-PU-PEU solution. No significant changes of the storage modulus (G') were observed until 31° C. indicating that it remained fluidic; a dramatic increase in the storage modulus were observed between 32-36° C. indicating the gelation, and the decrease in modulus occurred showing the phase separation.

Degradation of PEG-PU-PEG and PEG-PEU-PEG

For biodegradability, the copolymer solution was treated with both PBS solution and cholesterol esterase, and the molecular weights were measured every 7 days for 2 weeks. Each polymer was dissolved in both PBS solution and 400 U/ml of enzyme solutions with concentration of 5% (wt). 0.2 ml of fresh enzyme solution (2,000 U/ml) was added every three days to recover the enzyme activity.

The PEG-PU-PEG incubated in PBS solution did not show molecular weight (Mw) changes whereas 3.4% decrease in Mw was observed in enzyme solution in two weeks. For the PEG-PEU-PEG, 5.2% decrease in Mw was observed even in PBS solution. Much higher decrease in Mw, 29.8%, was observed in enzyme solution. Thus both PEG-PU-PEG and PEG-PEU-PEG have been proven to be biodegradable (Table 1).

TABLE 1

Degradation of PEG-PSeHDI-PEG and PEG-PSeSuHDI-PEG

|  | PBS | | | | E* (400 U/mg) | | | |
|---|---|---|---|---|---|---|---|---|
|  | 7 days | | 14 days | | 7 days | | 14 days | |
|  | Mw | DP | Mw | DP | Mw | DP | Mw | DP |
| PEG-PSeHDI-PEG Mw 6,211 DP 1.70 | 6,203 | 1.7 | 6,230 | 1.71 | 6,048 | 1.75 | 5,998 | 1.78 |

TABLE 1-continued

Degradation of PEG-PSeHDI-PEG and PEG-PSeSuHDI-PEG

|  | PBS | | | | E* (400 U/mg) | | | |
|---|---|---|---|---|---|---|---|---|
|  | 7 days | | 14 days | | 7 days | | 14 days | |
|  | Mw | DP | Mw | DP | Mw | DP | Mw | DP |
| PEG-PSeSuHDI-PEG Mw 9,824 DP 1.69 | 9,479 | 1.79 | 9,312 | 1.72 | 7.970 | 1.7 | 8,891 | 1.8 |

*E is cholesterol esterase from bovine pancreas (one unit will hydrolyze 1.0 nmol of cholesteryl oleate to cholesterol and oleic acid per minute at pH 7.0 at 37° C.)

Example 2

Reverse Thermal Gels in the Eye

To overcome perceived drawbacks in current ocular drug products, therapeutic agent-conjugated reverse thermal gels were developed which undergo temperature triggered sol-gel phase transition and form a gel at physiologically important temperature. Since the therapeutic agent conjugated reverse thermal gels can form gels by a simple injection in the vicinity of target area, loss of therapeutic agents can be minimized. It was hypothesized that controlled release would sustain the vitreous concentration of the therapeutic agents in the therapeutic range longer with reduced side effects and treatment frequency (FIG. 6) achieving higher therapeutic indices. The specific aim is to control the release of therapeutic agents using a functionalized reverse thermal gel that gels upon reaching body temperature. The release rate is controlled by varying the affinity between the gel and the therapeutic agents. The density of the delivery system is designed to approximately match that of the vitreous fluid.

Figures 6A, 6B:
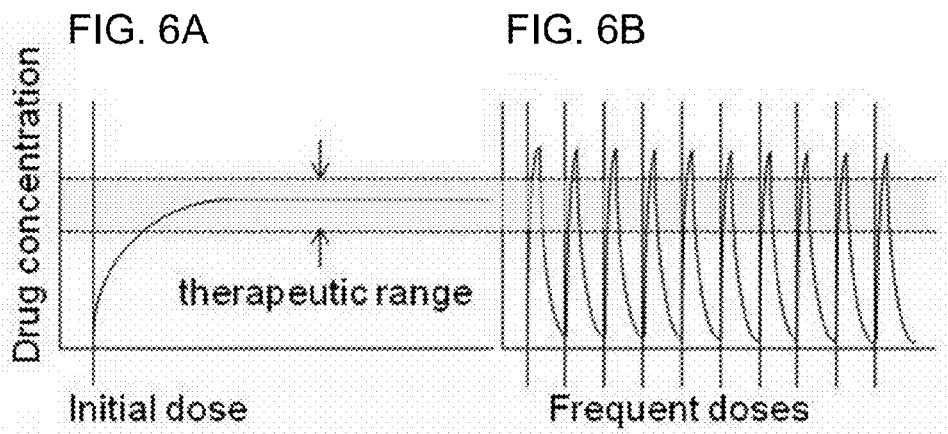
FIGS. 6A and 6B. Stimulated concentration profile of therapeutic agents in the vitreous fluid. (A) Proposed method that offers controlled release and a sustained concentration in the therapeutic range for a long period after one injection. (B) Current method that needs frequent injections.

FIG. 6 shows simulated concentration profile of the therapeutic agents in the vitreous fluid. (FIG. 6A) New method that offers controlled release and a sustained concentration in the therapeutic range for a long period after one injection. (FIG. 6B) Current method that needs frequent injections.

Because affinity is the main factor for the conjugations, most types of therapeutic agents can be conjugated to reverse thermal gels including antiangiogenic agents for macular degeneration, antibiotics for virulent inflammation, and growth factors for ocular wound healings.

Synthesis of Reverse Thermal Gel and Conjugation to Therapeutic Agents:

A biocompatible and biodegradable reverse thermal gel, PEG-Poly(serinol urethane)-PEG was designed and synthesized. This polymer gels at around 32° C. The gel was synthesized using N-Boc-serinol, hexamethylene diisocyanate and poly(ethylene glycol) as outlined in FIG. 1. The structure of this triblock copolymer is shown below.

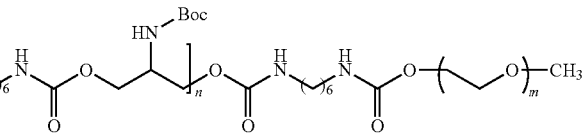

This copolymer was treated with 50% (v/v) of trifluoroacetic acid to deprotect the primary amine groups and produce ammonium groups. Therapeutic agents were mixed with 10, 15 and 20% (wt) of the ammonium-containing triblock copolymer in 0.2 ml of PBS. The negatively charged therapeutic agents, due to carboxylic acid groups, were complexed with positively-charged ammonium-containing triblock copolymer in the neutral solution by Coloumbic interaction. The affinity between therapeutic agents and the delivery polymer can lead to controlled release. The thermal behavior of therapeutic agent-complexed triblock copolymer was studied rheologically at the temperature range of 25-45° C.

Determination of Loading Efficiency:

The mixture of therapeutic agents and ammonium-containing triblock copolymer in PBS was raised to 37° C. to form a gel. 100 µl of PBS was added on top of the gel and agitated gently on an orbital shaker. The concentration of therapeutic agents in the supernatant was determined spectrophotometrically and chromatographically. The loading efficiency was calculated by the comparison of total concentration to supernatant one.

Figure 7:
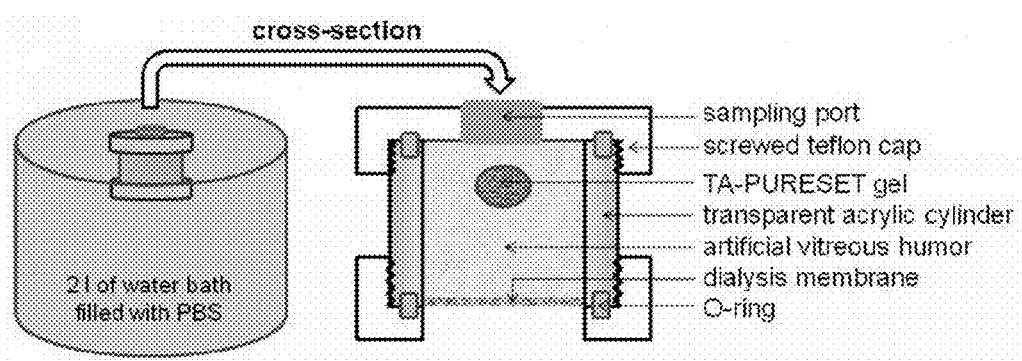
FIG. 7. (Left) The device for the study of the controlled release of therapeutic agents. (Right) the detailed cross-sectional view of the capsule as described in Example 2.
Figure 8:
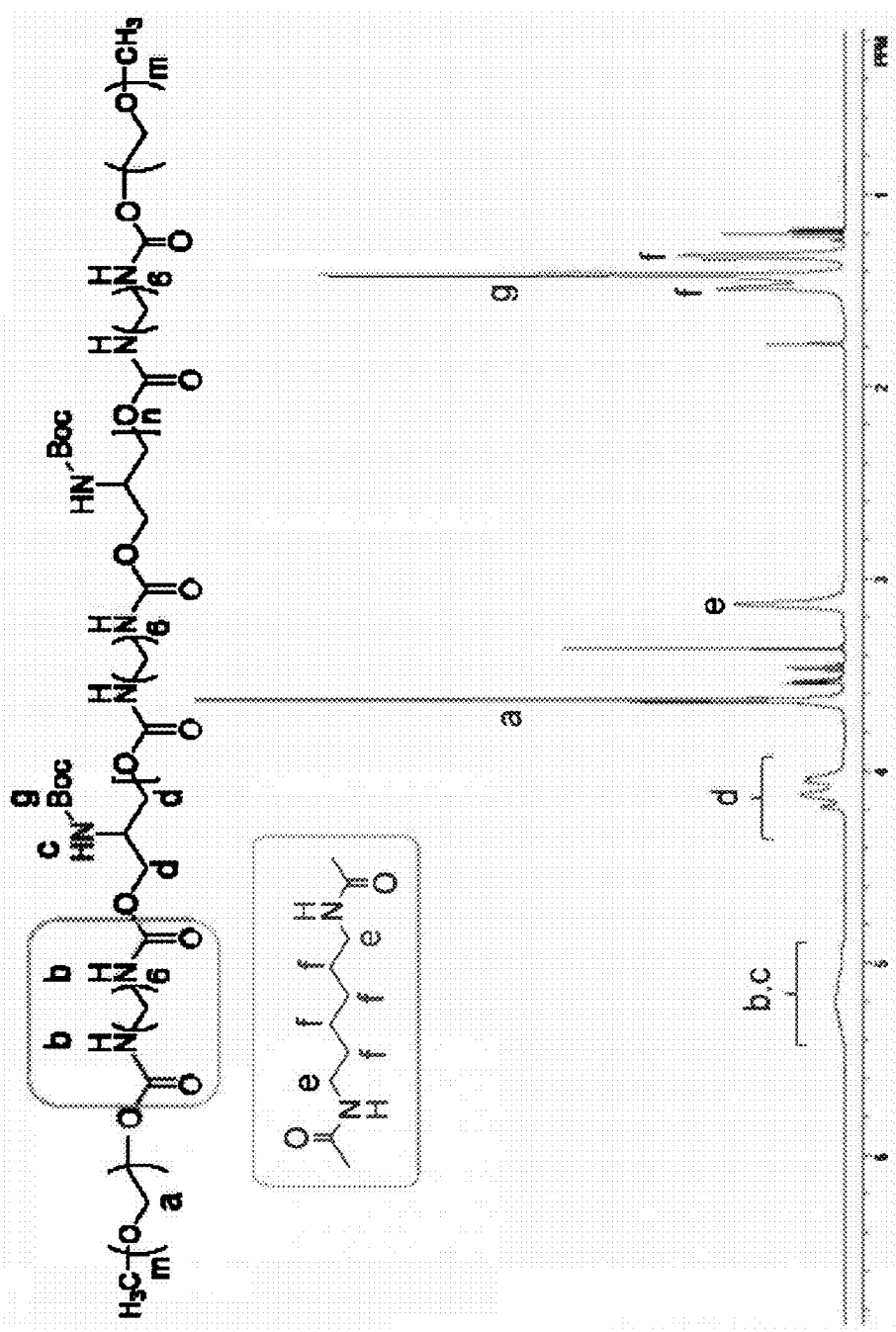
FIG. 8. 1H FTNMR spectra of poly (ethylene glycol)-poly (serinol hexamethylene urethane) (ESHU) in $CDCl_3$. The presence of a, e and g protons indicate the presence of PEG, polyurethane and tert-Butyloxycarbonyl (BOC)-protected amine groups in ESHU.

Biocompatibility and Biodegradability:

In vitro biocompatibility and biodegradability of the composition were studied. Biocompatibility studied according to ISO 10993-5 guidelines revealed excellent biocompatibility. In the presence of cholesterol esterase, the molecular weight of the polymer decreased 25% in 45 days. In PBS without any enzyme, the decrease was 2.5% in 45 days. The biocompatibility and biodegradability of the compositions were investigated in vivo using New Zealand white rabbits. A 0.5 ml of 20% therapeutic agent-complexed triblock copolymer solution was injected subcutaneously into four spots in the upper and lower back on both sides of the animal. In addition, the animals received 1 injection of 0.05 ml of 20% therapeutic agent-complexed triblock copolymer in the anterior segment of the eye. Biocompatibility also was tested in the posterior segment of the eye if the anterior tests show promising results. Rabbits were chosen to facilitate future efficacy and safety tests including intraocular pressure tests. The animals were euthanized at 1, 3, 7, 14 and 30 days. At each time point, the cutaneous and subcutaneous tissues surrounding the injection site were harvested. The tissues were fixed, stained, and examined by standard histological analysis for any signs of acute and chronic inflammation. Control was saline solution. For biodegradability evaluation, the size and dry weight of the therapeutic agent-complexed triblock copolymer gel was measured and compared to the original size and weight in phosphate buffered saline with and without choline esterase.
Control the Release of Therapeutic Agents:

The amount of therapeutic agents released is periodically measured spectrophotometrically and chromatographically in vitro using an artificial vitreous fluid. The release kinetics is measured at 37° C. in a custom made device (FIG. 7) with two compartments that mimic the eye and the body. The device will be kept under sterile conditions. The 2 liter PBS bath mimics the body. The plastic capsule mimics the eye. The dialysis membrane of the capsule allows mass transfer that simulates the mass transfer between the eye and the body. The device is filled with 7.5 ml (the volume of an adult eye is 7.2 to 7.5 ml) of artificial vitreous fluid. A 0.2 ml of the therapeutic agent-complexed triblock copolymer solution at ambient temperature is injected through the sampling port. Aliquots of the artificial vitreous fluid will be analyzed periodically between 1 and 120 days. FIG. 7. (Left) The device for the study of the controlled release of therapeutic agents. (Right) the detailed cross-sectional view of the capsule.

Example 3

Nerve Repair

When nerves are damaged slightly they can self-regenerate. However when the nerve defects or gaps are greater than 2 cm, surgical management will be a significant challenge. Many researchers have studied nerve regeneration by autologous grafts and tubular conduits, and biomaterials in which neurotransmitter, neural stem cell, and peptide are combined. These biomaterials are natural polymers such as collagen, fibrin, chitosan, and alginate and synthetic polymers. When these biomaterials are implanted into injured sites, most of them interact with invading neural cells by providing structural support, promote and eventually guide nerve growth (See, Yao, L., et al. Journal of Biomedical Materials Research Part A, J Biomed Mater Res. A. 2010 February; 92(2):484-92; Gao, J., et al. *Proc. Nat'l. Acad. Sci., U.S.A.*, Vol. 103, No. 45 (Nov. 7, 2006), pp. 16681-16686; and Mahoney, M J, et al. *Biomaterials* 27 (2006) 2265-2274). In one example, a composition described herein is deposited at a nerve growth site, such as a site of trauma to a nerve, so that it can serve as a nerve guide or scaffold for nerve regeneration.

Example 4

Treating Macular Degeneration with
Anti-Angiogenic Reverse Thermal Gel

Age-related macular degeneration (AMD) causes yellow deposits in the macula in the dry form, or choroidal neovascularization (CNV) and profound vision loss in the wet or exudative form. As the leading cause of the blindness in individuals older than 55 years, AMD affects more than 1.75 million people in the US and the number is expected to increase to 3 million by 2020. Current treatments for wet AMD rely on photodynamic therapy and injections of anti-angiogenic agents such as LUCENTIS®, AVASTIN®, or MACUGEN®. Photodynamic therapy (PDT) is based on the effect of oxygen radicals on the choroidal neovascular capillaries, where the dye is preferentially bound. However, PDT is only effective for some types of CNV and rarely improves vision. The current standard of practice is anti-angiogenic therapy based on the inhibition of vascular endothelial growth factor-A (VEGF-A) using the antibody (AVASTIN®) or antibody fragment (LUCENTIS®). However, because the half-life of protein-based drugs is short, the intravitreal injections are repeated frequently, sometimes monthly over several years. This creates a substantial treatment burden, requiring multiple injections and follow-up visits.

To ameliorate this burden a controlled release platform is used that can achieve a sustained therapeutic vitreous concentration of anti-VEGF for a long period of time. This will reduce treatment frequency, increase patient compliance and achieve a higher therapeutic index. Thus, the release of anti-angiogenic agents can be controlled using a transparent, biocompatible reverse thermal gel that gels upon reaching body temperature.

Synthesis of Reverse Thermal Gel:

A reverse thermal gel, PEG-Poly(serinol urethane)-PEG, a.k.a. ESHU (Scheme 1), was created using N-Boc-serinol, hexamethylene diisocyanate and poly(ethylene glycol).

Scheme 1. Chemical structure of ESHU.

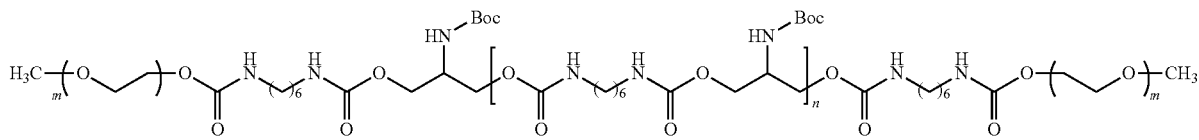

The chemical structures of ESHU were examined by 1H FTNMR analysis (FIG. 1). The methylene protons in PEG (a) and N-BOC-serinol (d) were confirmed at 3.65 and 4.0-4.2 ppm, respectively. The methylene protons adjacent to nitrogen in urethane functional groups (e) were observed at 3.17 ppm. The urethane protons bound to nitrogen and N-BOC-amine (b, c) were confirmed at 4.85-5.25 ppm. The signal at 1.42 ppm was assigned to methyl protons in BOC.

Figure 9A:
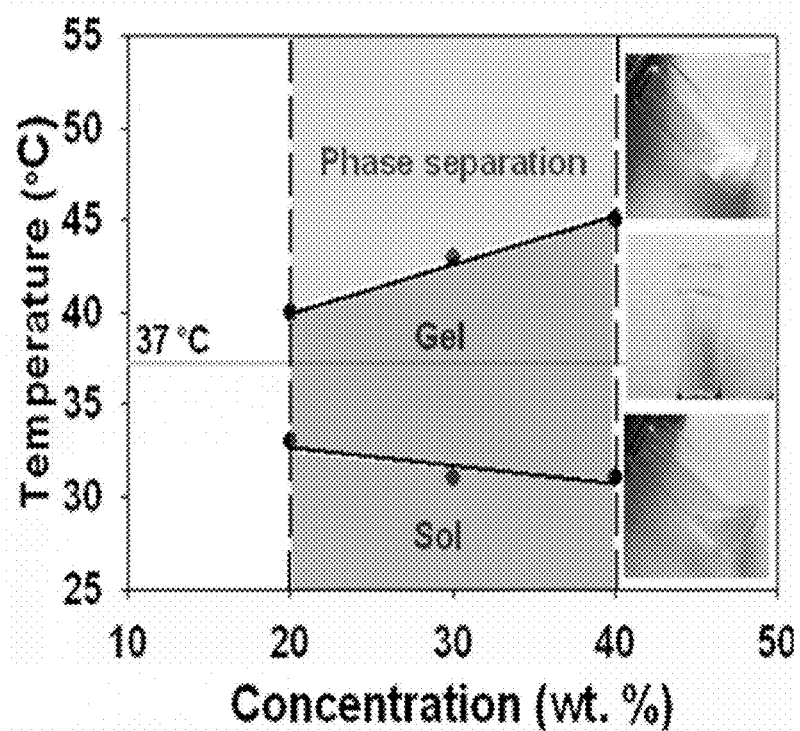
FIGS. 9A and 9B. Thermal behavior of ESHU. (A) The solutions underwent temperature triggered sol (red)-gel (blue) phase transition and remained gels at 37° C. Inset shows images of the polymer solution at 3 stages corresponding to (from the bottom) sol, gel, and phase separation. (B) G' changes with temperature at 20 and 30% (wt) concentrations.
Figure 9B:
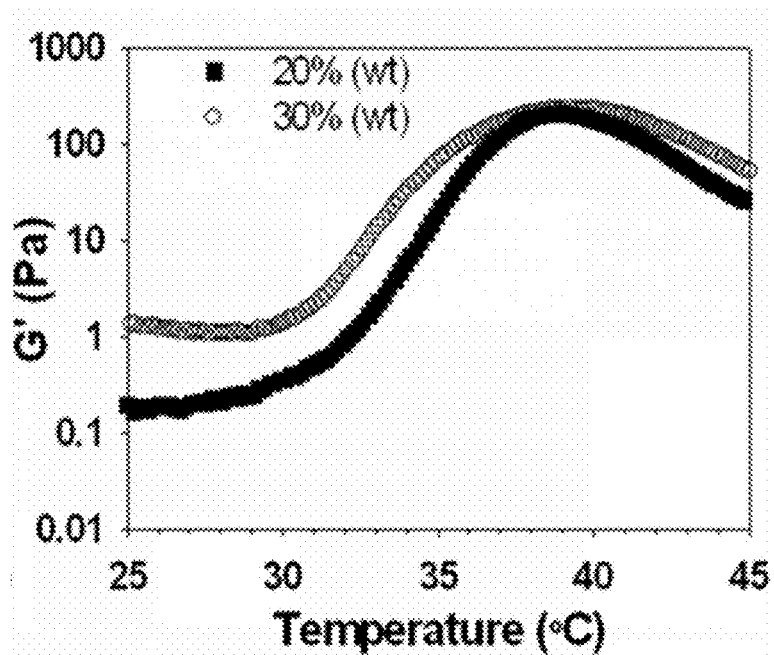
Figure 12A:
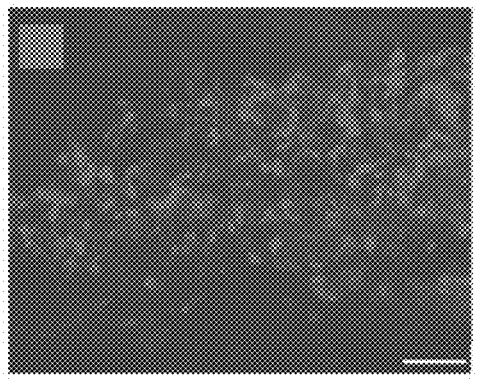
FIGS. 12A-12D.
Figure 12B:
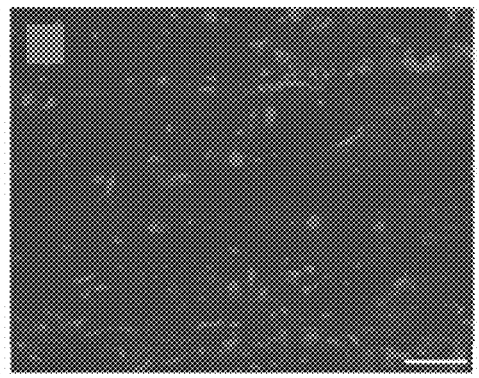
Figure 12C:
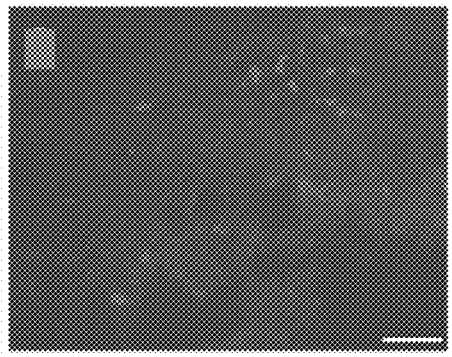
Figure 12D:
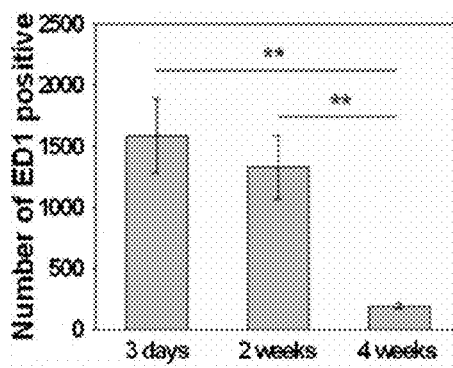

Thermal Behavior of Copolymer:

The solution of ESHU showed phase transition from solution to gel depending on temperature as well as concentrations. The solution remained gel (blue area) at body temperature in all tested concentrations (FIG. 9(A)). The consistent storage modulus (G') of ESHU indicates that the solution remained fluidic below 30° C. The sharp increase in G' between 32-40° C. indicates gelation (FIG. 9(B)).

In Vitro Biodegradability and Biocompatibility:

For biodegradability, ESHU was incubated in PBS and cholesterol esterase solution at 37° C. Degradation was determined by comparison of the molecular weights. ESHU showed a very slow degradation (2.5% in 45 days) in PBS, however, it was accelerated by cholesterol esterase (22% in 45 days) (FIG. 10).

In vitro biocompatibility was examined using primary bovine corneal endothelium cells. The cells were exposed to control (serum-free DMEM) and 15% (wt) ESHU gel in DMEM for 24 hr. The cells treated with Calcein AM showed no evidence of altered cellular morphology on microscopic examination (FIGS. 11, A and B). The viability was evaluated by immunofluorescent micropcry after staining with propidium iodide and Hoechst (FIGS. 11, C and D). Cytotoxicity was calculated as propidium iodide nuclei/total nuclei. No significant damage to cultured cells by ESHU was observed compared to the control (P>0.05, two way ANOVA).

In Vivo Biocompatibility:

In vivo biocompatibility was evaluated in Sprague Dawley rats. A near saturation concentration of ESHU (60% wt) was used to study the most severe host response. Subcutaneous implantation in rats revealed a well tolerated inflammatory response with moderate amount of ED-1 positive macrophages in the early stages, which largely resolved 4 weeks post-implantation (FIG. 12) indicating ESHU was biocompatible.

Figure 13A:
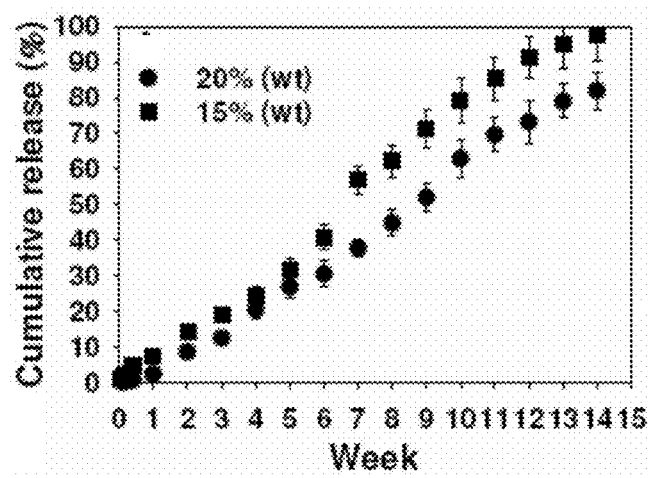
FIGS. 13A and 13B. Graphs showing the release profile of Avastin from ESHU gel. (A) With 0.5 mg of Avastin, 85.1% and 96.8%, and (B) with 1 mg, 75.4% and 81.3% were released from 20% and 15% ESHU gels respectively at 14 week post injection.
Figure 13B:
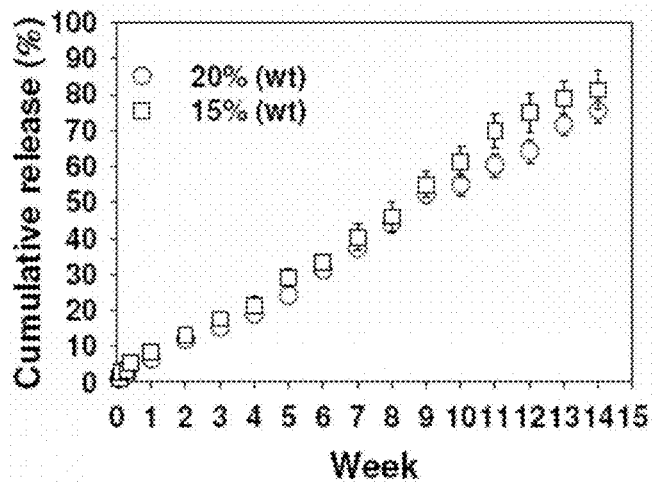

In Vitro Release of AVASTIN®:

AVASTIN® (Bevacizumab) was selected to represent anti-angiogenic agents because it is the most widely prescribed AMD treatment as it is inexpensive and effective. The release tests were performed in 7.5 ml of 1% (wt) hyaluronic acid solution at 37° C. to mimic vitreous fluid and under gyroscopic shaking to mimic human eye motion. Four formulas, 15 and 20% (wt) ESHU with 0.5 and 1 mg Avastin were used. The solution gelled immediately into a sphere upon injection into the 37° C. hyaluronic acid solution and quickly sank to the bottom indicating the delivery system will be out of the optical axis of the eye. The release of active AVASTIN® was measured by enzyme-linked immunosorbent assay (ELISA) according to manufacturer's protocol. The release was sustained and nearly linear without reaching plateau during the 14-week observation period post injection (FIG. 13). The release was more sustained at higher concentration because ESHU formed a more rigid gel at higher concentration. The half-life of free AVASTIN® in eyes is on the order of 7 to 10 days. The window of therapeutic concentration most likely depends on local conditions, such as the presence of blood or fluid in the neovascular complex, and the state of the vitreous gel into which the drug is injected. Therefore, the AVASTIN®-ESHU delivery system has three advantages over direct injection in that: 1. The therapeutic window is much longer, 2. The release is sustained, and 3. The injection frequency is greatly reduced.

Example 5

IKVAVS (SEQ ID NO: 21) Conjugated Reverse Thermal Gel Promotes Neurite Outgrowth Experimental Methods Synthesis of Reverse Thermal Gel Reverse thermal gel was synthesized. N-BOC-serinol (0.5 g, 2.62 mmol) was dissolved in 1 ml anhydrous DMF in a 25 ml round bottom flask at 90° C. under a nitrogen atmosphere. HDI (0.44 g, 2.62 mmol) was added slowly and the polymerization was performed. After 48 h, HDI (22 mg, 0.131 mmol) was added to facilitate the reaction. The polymerization was performed for 2 days. More HDI (0.88 g, 5.24 mmol) was added and the reaction mixture was stirred for 12 h. After cooling down to ambient temperature, the mixture was precipitated in excess anhydrous diethyl ether. The polymer was dissolved again in 2 ml anhydrous chloroform and poured into excess anhydrous diethyl ether to precipitate out the polymer. The purification process was carried out twice and the precipitates were washed in 100 ml of anhydrous diethyl ether overnight to remove unreacted HDI. The intermediate was obtained after drying at 45° C. under vacuum. As synthesized intermediate (1 g) and PEG (3 g, Mw: 550) were dissolved in 2 ml anhydrous DMF in a 25 ml round bottom flask and the reaction was performed at 90° C. for 12 h under a nitrogen atmosphere. After cooling down, the mixture was precipitated into excess anhydrous diethyl ether. After drying, the polymer was further purified with dialysis membrane in water at room temperature for 3 days. The dialyzed solution was freeze-dried and a transparent reverse thermal gel was obtained.

Conjugation of IKVAVS (SEQ ID NO: 21)

De-protection of reverse thermal gel: As synthesized gel (100 mg) was dissolved in 10 ml chloroform in a 50 ml round bottom flask. TFA (10 ml) was added and BOC de-protection was performed for 1 h at room temperature. After removing TFA and chloroform by rotary evaporation, the polymer was purified using dialysis in water at room temperature for 2 days. The dialyzed solution was freeze-dried and a pale yellowish solid ($NH_2$-GEL) was obtained.

Synthesis of IKVAVS (SEQ ID NO: 21) Conjugated Reverse Thermal Gel (IKVAVS-GEL):

I(BOC)K(BOC)VAVS(tBu)-OH (83 mg, 0.095 mmol) was dissolved in 23 ml anhydrous DMF in a 50 ml round bottom flask. DCC (21.6 mg, 0.105 mmol) solution in 1 ml anhydrous DMF was added slowly at 0° C. $NH_2$-GEL (50 mg, 0.19 mmol $NH_2$) solution in 1 ml anhydrous DMF was added with a catalytic amount of DMAP, which was stirred for 24 h at room temperature under a nitrogen atmosphere. After 24 h, acetic anhydride (19.4 mg, 0.19 mmol) and pyridine (75.1 mg, 0.95 mmol) were added which was then stirred for 24 h at room temperature. The cyclohexylurea was filtered off. After removing 90% DMF using rotary evaporator, it was poured into excess diethyl ether to precipitate out I(BOC)K(BOC) VAVS(tBu)-GEL. After drying, BOC was removed in 20 ml chloroform/TFA (50/50, v/v) mixture for 1 h at room temperature. After removing TFA and chloroform using rotary evaporator, the polymer was purified by dialysis in water at room temperature for 2 days. The dialyzed solution was freeze-dried and a pale yellowish solid, IKVAVS-GEL, was obtained.

Cell Culture

Cells, SH-SY5Y (ATCC, CRL-2266), were cultured in DMEM/F12 (1:1) medium with 10% fetal bovine serum (FBS), and 1% antibiotics. The cells were incubated in a humidified atmosphere with 5% $CO_2$ at 37° C. The medium was refreshed every three days until the cells reached 95% confluence. The cells were harvested from the petri dish by incubation in 1 ml of trypsin solution (0.25%) for 5 min, neutralizing with 5 ml of serum-supplemented medium, centrifugation and removal of supernatant. The cell pellets were resuspended in serum-supplemented medium and $5 \times 10^3$ cells was used immediately for 2D neuronal cell culture.

2D Neuronal Cell Culture

Fifty μl of each solution (15%, wt) of pure reverse thermal gel and IKVAVS-GEL was transferred into 96-well plate on 37° C. heating plate. After 5 min, cell suspension ($5 \times 10^3$ cells) in 150 μl of medium was added on top of the gel. For a control, the same number of cell suspension in 200 μl of medium was transferred into laminin coated 96-well plate. A 100 μl of medium was refreshed every two days. The cell growth was examined on a microscope. After 7-day culture, 10 μM of retinoic acid (RA) was added and neurite outgrowth was monitored on a microscope.

Results

3D Structure of IKVAVS-GEL

Figure 14:
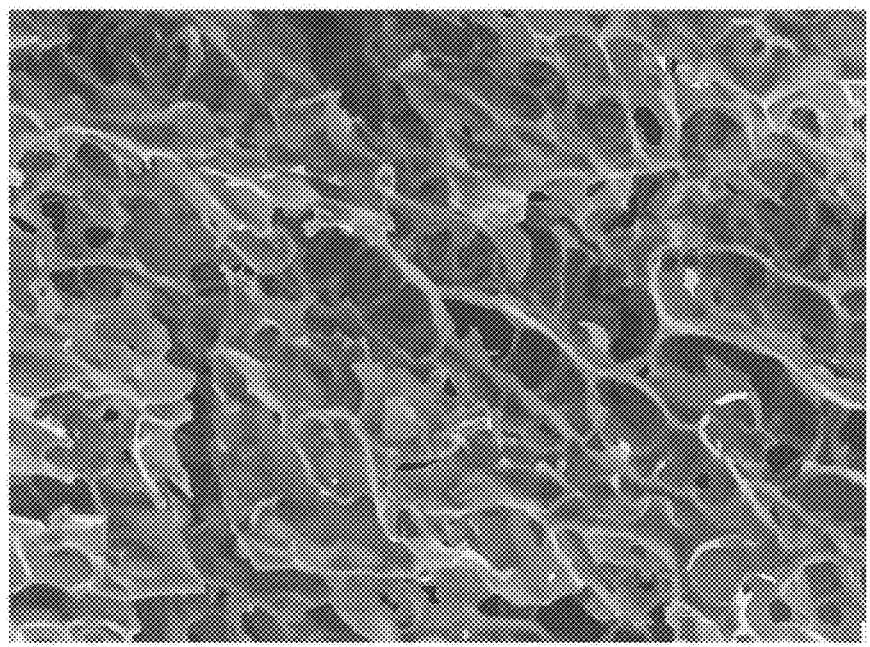
FIG. 14. 3D structure of IKVAVS-GEL.

To examine 3D structure of IKVAVS-GEL, 15% gel solution was placed in 37° C. water bath. Immediately after the gelation, it was placed in liquid nitrogen, frozen, and lyophilized. After drying, 3D structure was examined by SEM. Both the macro and micro pores were observed and they were interconnected each other (FIG. 14) which are good conditions for cell migration and nutrient supply.

2D Cell Growth and Neurite Outgrowth

Cells attached very well on laminin surface, a positive control, and few floating cells were observed (FIG. 15A). After 7-day culture, cells grew as clusters and formed many clumps which are typical morphology of growing SH-SY5Y (FIG. 15B). At day 7, 10 μM of RA (final concentration) was administered in one group and the differentiation of cells was compared after 14-day culture. Interestingly, some short neurite outgrowth was observed in a group without RA (FIG. 15C). However, much dense and longer neurite outgrowth was observed with RA (FIG. 15D).

Thus, laminin surface provided a good environment not only for cell growth but neurite outgrowth.

Cells seeded on pure reverse thermal gel did not attach well on the surface. Since the surface did not provide any bioactive cue, cells rather aggregated together (FIG. 16A) and slowly migrated from the aggregates (FIG. 16B). The differentiation was also not as extensive as the one on laminin surface. A few neurite outgrowth was observed without RA (FIG. 16C). They were not extended well even with RA (FIG. 16D). Thus, pure reverse thermal gel surface did not seem to provide a good environment for cell attachment and neurite extension. On the contrary, cells seeded on IKVAVS-GEL surface showed as good morphology and neurite outgrowth as on laminin surface. Cells attached well on the surface and did not form a big aggregate as pure reverse thermal gel (FIG. 17A). They formed many clumps after 7-day culture as seen on laminin surface (FIG. 17B). Neurite outgrowth without (FIG. 17C)/with (FIG. 17D) RA were much better than that on pure reverse thermal gel which is comparable with laminin surface. Thus, IKVAVS (SEQ ID NO: 1) conjugated reverse thermal gel provided a good cue for cell attachment and promoted neurite outgrowth.

Example 6

Transplantation of IKVAVS (SEQ ID NO: 21) Conjugated Reverse Thermal Gel Promotes Axon Regeneration and Functional Recovery after a Thoracic Spinal Cord Contusion in Adult Rats Studies are preformed to determine if the number of neurons with an axon projecting beyond a thoracic spinal cord contusion and hind limb motor performance after transplantation of IKVAVS (SEQ ID NO: 21) conjugated reverse thermal gel. IKVAVS (SEQ ID NO: 21)-conjugated reverse thermal gel is transplanted into a 3-day old contusion in the adult rat T9 spinal cord. Control rats receive ESHU or 'medium'. Survival is determined 1, 2, 4, and 8 weeks after transplantation. Biocompatibility, anatomical changes, cellular responses, axon regeneration, and motor function is investigated. KVAVS (SEQ ID NO: 21) conjugated reverse thermal gel promotes axonal regeneration in the contused adult rat spinal cord, and recovery of hindlimb motor function after a contusion of the rat thoracic spinal cord is proportional to the number of regenerated axons into the caudal cord.

Methods

Rats: Adult female Sprague Dawley, 180-200 g. Total number of rats is 63. Three groups are as follows: pure reverse thermal gel, IKVAVS (SEQ ID NO: 21) conjugated reverse thermal gel, and medium only, with 20 rats each (n=3 for 1, 2, and 4 weeks; n=12 for 8 (+1) weeks).

Contusion: T9; 1H-impactor at 200 kDyn.

Implantation: Five (5) μL, pure reverse thermal gel, IKVAVS (SEQ ID NO: 21) conjugated reverse thermal gel, or medium into mid-point of 3-day old contusion.

Survival: 1, 2, 4, and 8 (+1 for tracing) weeks after transplantation.

Motor testing: Only in 8 (+1) week survival group. BBB (includes BBB-subscore) (before (3 times) and 1, 3 days after injury, and 3, 7 days, and then weekly after transplantation); foot print and horizontal ladder walking (before (3 times) and 3 days after injury, and 3 days and 1, 2, 4, 8 weeks after transplantation).

Retrograde tracing: At 8 weeks after transplantation, 1.2 μl 2% FB is injected in the spinal cord 7 mm caudal to the contusion epicenter.

Histology: 4% paraformaldehyde fixation. Cryostat sections of spinal cord (transplant plus 5 mm rostral and distal cord: 20 μm, horizontal, 10 series) and brainstem and cerebral cortex (40 μm, transversal, 10 series).

Analyses (*=Main Outcome Measures. Others are to Support)

Analysis of Axon Regeneration:
1. Quantify FB-labeled neurons in spinal cord rostral to transplant, brainstem, cortex.
*2. Quantify serotonergic and dopaminergic axons caudal to transplant.

Analysis of Motor Function:
*1. Overground locomotion (BBB)+higher motor functions (BBB subscore).
*2. Sensorimotor performance (horizontal ladder walking).
*3. Locomotion pattern: stride length, base of support, and angle of rotation (foot print).

Analysis of Cellular Changes:
1. Scar (ICC for astrocytes and CSPG)
2. Cell architecture (Nissl staining).
3. Neuron presence (ICC for NeuN)
4. Inflammation (ICC for macrophages)

Analysis of Anatomical Changes:
1. Tissue sparing (using Nissl-stained sections).
*=main outcome measures. Others are to support.

Example 7

Testing of Intraocular Dosage Form in Rabbits

Human eyes are often exposed to various risks of ocular diseases. They can be an age-related such as macular degeneration; virulent inflammations by foreign bodies such as endophthalmitis; and systemic side effects such as diabetic retinopathy, macular edema, and retinal vein occlusion. Intravitreal drug injections are the most effective way to maximize drug concentrations in the eye and reduce the loss whereas limiting systemic exposure. However, the effective management of chronic ocular conditions requires long-term frequent local administrations with over- and underdoses. Those repeated intravitreal injections are not only invasive and inconvenient for patients, but they may also greatly increase the risk of complications such as intraocular pressure elevation, cataracts, and retinal detachment.

To overcome these drawbacks therapeutic agents are conjugated with reverse thermal gels (TA-ESHU) which undergo temperature triggered sol-gel phase transition and form a gel at body temperature. Since the TA-ESHU can form gels by a simple injection in the vicinity of target area, the loss of therapeutic agents can be minimized. The controlled release sustains the vitreous concentration of the therapeutic agents in the therapeutic range longer with reduced side effects and treatment frequency achieving higher therapeutic index. The release rate is controlled by varying the affinity between the gel and the therapeutic agents. The density of the delivery system is designed to approximately match that of the vitreous fluid.

Sample sizes are selected based on a power analysis with a significance level $\alpha$ of 0.05 and a power $(1-\beta)$ of 0.85. Assuming a typical standard deviation of 35% and desiring to detect a 33% difference in means, we obtain a sample size of 10 using MiniTab (Statistical Software). In case the standard deviation assumption is proven to be invalid a posteriori, an adaptive sampling rate for the testing will be employed.

Therapeutic agent-conjugated polymer compositions are injected in three separate parts of the animal's eye, upper back, and lower back. Each part has two samples. For eye, a left eye and a right eye. For upper back, a left side and a right side. For lower back, a left side and a right side. Then each animal has two samples for the biocompatibility and biodegradability. Five animals are used for each time point. Then, the sample size in each time point is 10 (5×2=10).

Preparation: All rabbits are used after at least three days post arrival. For each group of studies: 5 survival times×6 rabbits/survival time (5 for test, 1 for control)=30 rabbits.

Pre-operative evaluation and preparation: Pre-op evaluation and preparation includes weighing the rabbit and recording the body weight.

For biocompatibility study through intravitreal injection: 0.05 ml of 20% and 30% therapeutic agent-conjugated reverse thermal gel solution will be injected in the eye. In one example, the therapeutic agent is AVASTIN®. Typically the injection of thermal gel has been done under anesthesia condition for intravitreal injection. Rabbits are anesthetized using either sodium pentobarbital or a mixture of ketamine and xylazine. The volume of thermal gel for intravitreal injection has been in the range of 50-100 μl. The minimum volume (50 μl) is injected. A 25 gauge needle is used for the injections. After euthanization with 120 mg/kg sodium pentobarbital at 1, 3, 7, 14 and 30 days, the surgical eye including the upper eyelids are removed. The surgical eye is fixed in 4% formaldehyde, stained, and examined by standard histological analysis for any signs of acute and chronic inflammation. Control is 0.05 ml of saline solution.

For intraocular pressure (IOP) measurement: The measurement of IOP is performed preinjection and at 1, 3, 7, 14 and 30 days post-injection using tonometer by distributor's protocol.

At the end of the studies cells are isolated for future biocompatibility and stromal cell differentiation capability tests of therapeutic agent-conjugated reverse thermal gels as follows:

Animals are euthanized following survival times and tissue and cells are harvested.

The rabbits are examined and its response to gentle palpation or handling of any presumed painful areas (e.g., the site of surgery) is assessed. The rabbit is weighed every 24 hours, and the cage is examined for signs of normal or abnormal urination or defection.

The following criteria is used to determine full recovery from surgery: 1) locomotive and grooming behavior equivalent to presurgical state, and 2) eating and drinking equivalent to presurgical state. Postoperative analgesia will be provided by injections of Ketoprofen 12 hours after surgery, and once per two days afterward (if needed). Rabbits will be monitored closely (every 12 hours) for any signs of distress (vocalization, decrease in food consumption, etc.). If rabbits scratch or bite their injection sites, if the skin becomes reddened or if dermatitis develops, or rabbits lose more than 20% of their immediate post-operative body weight, they will be euthanized. Body weight will be monitored every 24 hours.

For intravitreal injection, some clinical signs may appear when animals receive injections, such as scratching their injection sites, increase in intraocular pressure, weight loss. Complications are not expected in any case. If rabbits keep scratching their intravitreal injection sites, if the intraocular pressure keeps increasing, or rabbits lose more than 20% of their immediate post-operative body weight, they are euthanized. Body weight is monitored every 24 hours.

Example 8

Models of Spinal Cord Injury

A. Transection

To determine the reverse thermal gels' efficacy in functional nerve regeneration, 10 rats per time point are used. Histological, behavioral, and electrophysiological assessment is performed at 2, 5, and 8 weeks for spinal cord regeneration after surgery. If 10 animals are used per condition, then 30 animals are necessary to fulfill the study (3×10=30). 10 rats are used per condition. Power analysis is performed using MiniTab Software (Statistical Software). Ten types of polymer composition are tested, so 300 animals are necessary to fulfill the study (10×30=300).

Negative control is "injury only" for CNS nerve regeneration. Positive controls are not appropriate for the following reasons. There is no current treatment that can lead to functional recovery, so there is no positive control. Therefore, two groups of 20 rats in total are required for the first time study, therefore 320 animals are necessary to fulfill the study (10× 30+20=320). A total of 60 animals (three time points, 10 animals/time point) for each polymer conduit will be sacrificed at three time points for histological, behavioral, and electrophysiological assessment on nerve regeneration.

Preparation: All animal are used after at least three days post arrival. The animals are prepared by removing hair from the surgical site, and the surgical sites are sterilized with an appropriate skin disinfectant such as Betadine. For each study: three survival times×10 animals/survival time are used, totaling 30 animals. Pre-operative evaluation and preparation includes weighing the animal and recording the body weight. Aseptic surgical technique is ensured by performing the surgeries in a disinfected suite. For direct Spinal Cord Injury:

1. The rats are anesthetized using sodium pentobarbital (45-50 mg/kg) given either intraperitoneally (using a 25-26 gauge needle) under brief anesthesia induced with 5% isofluorane.
2. Opthalmic ointment is used on the eyes to prevent corneal abrasion.
3. The hair down the back over the spine is removed with electric clippers.
4. The area is cleaned with chlorhexaderm and then with 70% ethanol.
5. The rat is draped with sterile surgical drapes.
6. An incision is made over the thoracic region of the spinal cord T6-T11.
7. The muscle is cut on both sides of the spine.
8. A double laminectomy is performed removing T9 and T10.
9. The dura mater is excised longitudinally.
10. To sever the dorsal corticospinal tracts, microscissors previously marked at 1.5 millimeters are used to cut down through the dorsal columns until we reach the pre-determined depth. The length of the cavity is 2 millimeters.
11. The reverse thermal gel is injected into the lesioned cavity.
12. In order to stop bleeding during surgery, Tisseel Fibrin Sealant, a product made by Baxter, is applied. It is sterile and non-pyrogenic. The literature contains many references to the use of this product in rats indicating that it is safe and effective in this species. Tisseel is mixed according to package directions and applied topically to bleeding areas during surgery. No side effects are expected.

13. The dura is sutured and the muscle and skin will be closed in layers.
14. The rat recovers on a heating pad or under a heat lamp.
15. Animals are monitored for up to 8 weeks. These rats are expected to maintain the ability to urinate and defecate on their own without having a person manually express. The rats also are expected to be able to walk around on their fore and hind limbs on their own accord; however, in the first 48 hours, they are expected to go through spinal shock and should not be able to have full use of their hind limbs.
16. Ketaprofen is administered post-operatively for pain that the rat may experience if needed.
17. Suture and/or wound clips are removed 10-14 days post-operatively).

Rodent euthanasia and tissue harvest: Following post-inoculation survival times of each time point, the animals are be anesthetized with 50 mg/kg sodium pentobarbital intraperitoneally, and tissue is harvested and transfer into buffered aldehyde solution. Tissue will be harvested after complete euthanasia.

B. Compression

Alternately, another spinal cord injury model is performed according to this protocol. No other change is made to this protocol. In the original protocol, transection to create spinal cord injury will be utilized. An alternative spinal cord injury model to transection is a clip compression method is used to create spinal cord injury as the second model in the protocol. Because the "transection procedure" is expected to cause more severe injury to spinal cord as compared with "compression injury model," the effect of polymers through "compression injury model" at first is evaluated, then two of the most effective polymers are chosen for the evaluation in "transection model." As with the first protocol, three time points are set, with ten rats per time point, totaling 60 rats for this modified protocol.

In the surgical procedure, a 30-40 mm dorsal midline incision is made and laminectomy is performed at T6-T11 level. Compressive injury is produced by transient extradural application of a modified iris clip, which exerted a force of about 90 gram on the spinal cord for 2 min. After removal of the clip, the dura in the lesion area is incised, and spinal cord is exposed, then the prepared polymer is administered in the lesion. Dura and skin incision is closed, and the animal is returned to cages with highly absorbent soft bedding in pairs (to reduce isolation-induced stress).

Immediately following surgery and during recovery from anesthesia, rats recover under a heat lamp to raise the recovery area ambient temperature to between 85-90° F. Each animal is examined and assessed for its response to gentle palpation or handling of any presumed painful areas (e.g., the site of surgery, the site of lesion). The animal is weighed every 24 hours, and the cage is examined for signs of normal or abnormal urination or defection.

The following criteria is used to determine full recovery from surgery: 1) locomotive and grooming behavior equivalent to presurgical state, and 2) eating and drinking equivalent to presurgical state. Postoperative analgesia is provided by injections of Ketoprofen 12 hours after surgery, and once per two days afterward. Animals are monitored closely (every 12 hours) for any signs of distress (vocalization, decrease in food consumption, etc.). Furthermore, the health of the animals following surgery is monitored for adverse signs due to the effects of the injured nerves. If rats scratch or bite their implants, if they lose hair over their implants, if the skin becomes reddened or if dermatitis develops, if incisions do not heal or an exudate develops or rats lose more than 20% of their immediate post-operative body weight, they are euthanized.

Example 9

Materials and Methods for Examples 10-14

Poly(ethylene glycol)-poly(serinol hexamethylene urethane) (ESHU) is a reverse thermal gel with good biocompatibility. ESHU is a copolymer with two hydrophilic poly(ethylene glycol) blocks flanking a hydrophobic poly(serinol hexamethylene urethane) block (Park et al., Biomaterials 32(3), 777-786 (2011)). Oxidation of polyurethane (Christenson et al., J. Biomed. Mater. Res. A 70(2), 245-255 (2004); Schubert et al., J. Biomed. Mater. Res. A 29(3), 337-347 (1995)) provides ESHU with antioxidant capacity. ESHU dissolves in water and undergoes phase transition with increasing temperatures to form a physical gel at 37° C. (Par et al., supra), which makes it especially practical for treatment of closed injuries (Oudega et al., Acta Physiol. 189(2), 181-189 (2007)).

It was hypothesized that the antioxidant capacity of ESHU protects intraneural cell transplants from oxidative stress-related death leading to improved repair. This was tested in vitro using bone marrow stem cell (BMSC) cultures determining the effects of ESHU on BMSC survival and in vivo using an adult rat model of spinal cord contusion assessing BMSC transplant survival, inflammation, anatomical restoration, and functional recovery.

In an adult rat spinal cord contusion model it was investigated whether poly(ethylene glycol)-poly(serinol hexamethylene urethane) (ESHU) would enhance BMSC transplant survival leading to improved repair. ESHU promoted survival of BMSCs under oxidative stress in vitro and in the injury epicenter compared with controls, which received BMSC in phosphate-buffered saline. ESHU-mediated BMSC survival increased tissue sparing in the damaged spinal cord segment and hindlimb motor and sensorimotor recovery. This data indicates that ESHU-induced antioxidation enhances BMSC transplant survival leading to increased neuroprotection associated with behavioral improvements. It was demonstrated that the therapeutic efficacy of intraneural BMSC transplants depends on their extent of survival.

Ethics and Surgical Approval.

Rats were kept within a double-barrier facility in standard rat cages with continuous supply of fresh air, water, and food.

Transplant Preparation.

Figure 18A:
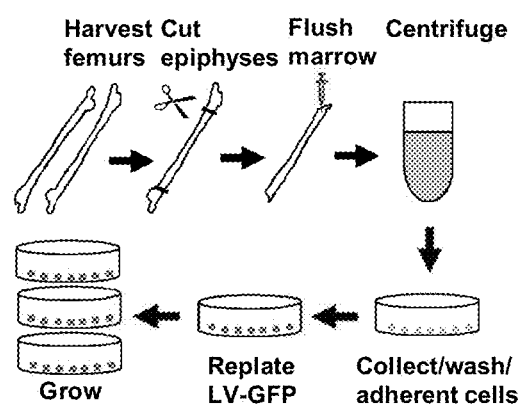
FIGS. 18A-18C. Schematic representation of a BMSC transplant preparation and ESHU. (A) Isolation and transduction of bone marrow stromal cells. Plastic-adherent cells from femurs of adult Sprague-Dawley rats were collected, lentivirally transduced with green fluorescent protein, and passaged four times before used for transplantation. (B) Green fluorescent protein-expressing bone marrow stromal cells in culture. Small panels show examples of cultured BMSC morphologies. (C) Structural formula of ESHU with the urethane bond in gray box. Bar=50 μm in b and 25 μm in panels below.
Figure 18B:
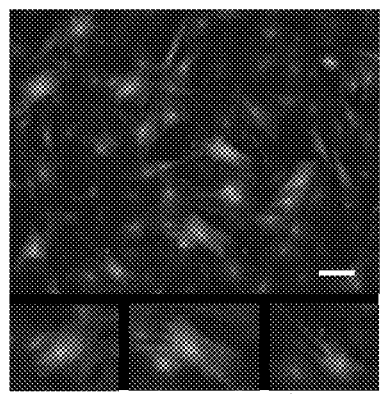

BMSCs were harvested from femurs of female adult Sprague Dawley rats according to a previously described protocol (FIG. 18A) (Ritfeld et al., 2012, supra, Nandoe Tewarie et al., 2009, supra). Isolated cells were grown in Dulbecco's Modified Eagle Medium (DMEM, Sigma-Aldrich, Allentown, Pa., USA) with 10% fetal bovine serum (Mediatech, Manassas, Va., USA) and 1% penicillin/streptomycin (Invitrogen, Grand Island, N.Y., USA). To enable detection after transplantation, first passage cells were transduced to express green fluorescent protein (GFP) using lentiviral vectors (FIG. 18B) (Ritfeld et al., 2012, supra, Nandoe Tewarie et al., 2009, supra). Fourth passage cells positive for the BMSC markers, CD90 and CD105 and negative for blood cell markers, CD34, CD45 and HLA-DR (Ritfeld et al., 2012, supra; Conget et al., J. Cell. Physiol. 181(1), 67-73 (1999)) were used for the studies.

ESHU.

Figure 18C:
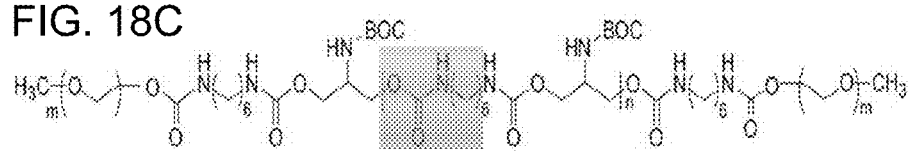

ESHU (FIG. 18C) was prepared (Park et al, Biomaterials 32(3), 777-786 (2011)). In brief, polyurethane blocks were synthesized by melting N-BOC-serinol (Sigma-Aldrich) under nitrogen and slowly adding hexamethylene diisocyanate (HDI; TCI America, Wellesley Hills, Mass., USA) to initiate polymerization via urethane bonds. Both ends of polyurethane were capped with an isocyanate group using additional HDI and then dissolved in anhydrous dimethylformamide. Diethyl ether (Fisher Scientific, Pittsburgh, Pa., USA) was used to precipitate out the polymer and remove unreacted hexamethylene diisocyanate. Polyethylene glycol (Alfa Aesar, Ward Hill, Mass., USA) was coupled onto the polyurethane blocks under nitrogen, dissolved in dimethylformamide (EMD, Gibbstown, N.J., USA), and precipitated in and washed with diethyl ether. For purification, ESHU was dissolved in water and dialyzed (3500 MWCO) for 48 h and finally freeze-dried. In these studies, a 16% w/v ESHU solution in phosphate-buffered saline (PBS; pH 7.4) was prepared and sterile-filtered before use.

Assessment of the Protective Effect of ESHU.

Figure 19A:
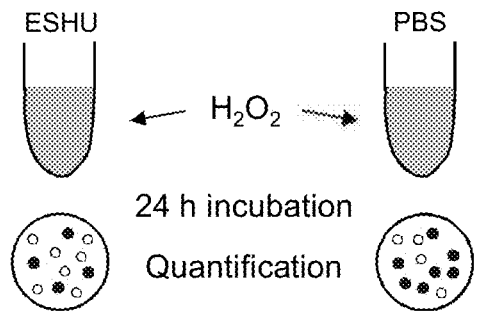
FIGS. 19A-19C. ESHU protects bone marrow stromal cells in suspension and scavenges hydrogen peroxide in vitro. (A) Schematic representation of in vitro assay of ESHU's ability to protect bone marrow stromal cells from hydrogen peroxide ($H_2O_2$)-induced death. (B) Bar graph showing that cell survival from $H_2O_2$-induced oxidative stress was better in ESHU than phosphate-buffered saline (PBS). (C) Bar graph showing that ESHU scavenged $H_2O_2$ in PBS. Error bars in bar graphs display standard error of the mean (SEM) and asterisks indicate $p<0.05$.

To quantify ESHU's protective ability BMSCs were kept in vitro under oxidative stress, which contributes to intraneural cell transplant loss (Siriphorn et al., *J. Neurochem.* 115(4), 864-872 (2010)). A total of $4 \times 10^5$ cells were incubated in 100 µl ESHU or PBS with 200 µM hydrogen peroxide ($H_2O_2$; Sigma-Aldrich) for 24 h at 37° C. (FIG. 19A). Then, 100 µl Trypan Blue (Sigma-Aldrich) was added and viable (Trypan Blue-negative) cells were quantified in a hematocytometer and expressed as a percentage of all counted cells. Results from three independent studies were averaged.

Quantification of ESHU's Antioxidant Ability.

ESHU's ability to scavenge $H_2O_2$ relative to PBS was measured using a $H_2O_2$ quantification kit (National Diagnostics, Atlanta, Ga., USA) which colorimetrically measures Xylenol Orange-Ferric iron complex resulting from $H_2O_2$-mediated oxidation of ferrous iron. The linear standard curve of this assay is 15-100 ng/ml. Thirty ng/ml $H_2O_2$ (Sigma-Aldrich) was added to ESHU or PBS which was kept in reagent buffer for 30 min following the manufacture's guidelines. Absorbance was measured (Victor 2V 1420; Perkin-Elmer, Waltham, Mass., USA) and the values from three independent studies were averaged.

Surgical Procedures.

A model of adult rat spinal cord contusion (Kakulas, *J. Spinal Cord Med.* 22 (2), 119-124 (1999)) was used. Female adult Sprague Dawley rats (200 g, n=70; Charles Rivers Laboratory, Wilmington, Mass., USA) were anaesthetized using Ketamine (60 mg/ml IP; Butlerschein, Dublin, Ohio, USA) and Dexdomitor (0.5 mg/kg IP; Pfizer, New York, N.Y., USA) (Ritfeld, G. J. et al. *Cell Transplant.* 21(7), 1561-1575 (2012); Nandoe Tewarie, et al. *J. Neurotrauma* 26(12), 2313-2322 (2009)). The tenth thoracic spinal cord segment was contused using a force of 200 kDyne (Infinite Horizon IH-0400 impactor; Precision Systems and Instrumentation, LLC, Versailles, Ky., USA) (see, for example, Ritfeld et al., 2012, supra and Nandoe Tewarie et al., 2009, supra). The wound site was rinsed with sterile PBS with 0.1% gentamicin (VWR, Radnor, Pa.), the muscles were sutured in layers, and the skin was closed with Michel wound clips (Fine Science Tools, Foster City, Calif., USA). All rats included in the studies had an impact within 5% of the intended force resulting in a 0.9-1.8 mm spinal cord compression and a Basso-Beattie-Bresnahan (BBB) (Basso et al., *J. Neurotrauma* 12, 1-21 (1995)) score ≤1 at day 1 and ≤5 at day 3 post-impact. Three days after injury, rats were anaesthetized and injected into the contusion epicenter with 5 µl ESHU or PBS with $5 \times 10^5$ BMSCs, or ESHU or PBS only.

Post-Surgery Procedures.

Antisedan (1.5 mg/kg, SQ; Pfizer) was used to reverse the effects of Dexdomitor (Ritfeld et al., supra and Nandoe Tewarie et al., supra). Gentamicin (6 mg/kg IM; VWR), Rimadyl (5 mg/kg SQ; Pfizer), and Ringer's solution (10 ml SQ on surgery day, 5 ml SQ thereafter; Butlerschein) were administered daily for the first three days post-injury. After the intraspinal injection at three days post-injury, the rats received gentamicin for four days and Ringer's and Rimadyl for three days (Ritfeld et al., supra and Nandoe Tewarie et al., supra). Bladders were manually emptied twice daily until reflex voiding occurred. Rats were monitored daily throughout the studies. Rats were fixed at 15 min, one, four, or six weeks after injection. All rats survived without requiring pain or distress treatment.

Motor Function Assessment.

Overground walking ability was assessed using the BBB test (Basso et al., supra) weekly for six weeks post-injection. Rats were tested for 4 min by two testers unaware of the treatments. Rats were familiarized with the open field and baseline values were determined before surgery. Scores were averaged per test group. Higher motor functions were assessed for six weeks post-injection using the BBB subscore (Lankhorst et al., *Neurosci. Res. Comm.* 24, 135-148 (1999)) as previously described (Ritfeld et al., supra). Scores were averaged per test group. Sensorimotor function of the hind limbs was assessed before (baseline) and at six weeks post-injection using horizontal ladder walking (Ritfeld et al., supra and Nandoe Tewarie et al., supra; Kunkel-Bagden et al., *Exp. Neurol* 116, 40-51 (1992)). Slips of the foot and part of lower leg and slips of the full leg were counted and expressed as a percentage of the total number of steps. Scores were averaged per test group.

Histological Procedures.

Rats were anaesthetized and transcardially perfused with 300 ml PBS followed by 400 ml 4% paraformaldehyde (Sigma-Aldrich) in PBS. Spinal cords were dissected, post-fixed overnight in the same fixative, and transferred to 30% sucrose (Fisher Scientific) in PBS for 48 h. A 12 mm-long spinal cord segment centered at the injury epicenter was cut in 20 µm-thick horizontal cryostat sections (CM 1950; Leica Biosystems, Buffalo Grove, Ill., USA). Every twelfth section was stained with cresyl violet (0.5%; Sigma-Aldrich) for cytoarchitecture analysis and spared tissue volume assessment. Other section series were used for immunocytochemistry. Sections were analyzed using an Axio Observer Z1 fluorescent microscope (Zeiss, Thornwood, N.Y., USA) with STEREOINVESTIGATOR® (MicroBrightField, Inc., Williston, Vt., USA).

Immunocytochemistry.

Sections were incubated in 5% normal goat serum (Vector Labs, Burlingame, Calif., USA) and 0.03% Triton X-100 (Sigma-Aldrich) in PBS for 1 h followed by the primary antibody for 2 h at room temperature and then overnight at 4° C. Rabbit polyclonal antibodies against glial-fibrillary acidic protein (GFAP) were used to detect astrocytes (1:200; Dako North America, Inc., Carpinteria, Calif.). Mouse monoclonal antibodies against ED1 were used to detect macrophages (1:100; Millipore, Temecula, Calif.). After washing twice in PBS for 20 min, sections were incubated with goat-anti-rabbit and goat anti-mouse ALEXAFLUOR® 594 (1:200; Life Technologies, Grand Island, N.Y., USA) for 2 h at room temperature. DAPI (0.2 µl/ml; Sigma-Aldrich) was used to stain nuclei. Sections were covered with glass slips in fluorescent mounting medium (Dako North America, Inc.) and stored at 4° C.

Quantification of Transplanted Cells.

STEREOINVESTIGATOR® (MicroBrightField, Inc.) was used to stereologically determine the numbers of GFP-positive BMSCs in the injury site (Nandoe Tewarie et al., supra; Boyce et al., *Toxicol. Pathol.* 38 (7), 101110-101125 (2010)) at seven days post-transplantation in every twelfth section by personnel blinded to the treatment groups. Sections were 240 µm apart spanning the width of the spinal cord. In every section the area containing GFP-positive cells was outlined manually at 2.5× magnification and covered with a 250×250 µm grid. At 60× magnification with oil immersion, GFP-positive cells with a discernible DAPI-stained nucleus were marked using the optical fractionator with a 60×60 µm counting frame (Ritfeld et al., 2012, supra and Nandoe Tewarie et al., 2009, supra; Boyce et al., supra). The numbers of GFP-positive cells, expressed as a percentage of the number of transplanted cells (±SEM), were averaged per test group.

Quantification of Macrophages.

ED1-immunoreactive macrophages in the injury site were quantified at one and four weeks post-transplantation in every twelfth section by persons blinded to the treatment groups using ImageJ Software as described previously (Ritfeld et al., *Neuroreport* 21(3), 221-226 (2010)). Numbers were averaged per test group (±SEM).

Measurement of Nervous Tissue Sparing.

Cresyl violet-stained sections of rats that survived for four weeks post-injection were used to determine the volume of spared tissue in the damaged spinal cord segment using the Cavalieri estimator function of STEREOINVESTIGATOR® (MicroBrightField, Inc.) (Ritfeld et al., supra; Boyce et al., supra). Analysis was performed by personnel blinded to the test groups. The Gundersen Coefficient of Error was <0.05 for all measurements. The volume of spared tissue was expressed as a percentage of the volume (±SEM) of an equally-sized comparable uninjured spinal cord segment and averaged per test group.

Statistical Analysis.

Two-tailed Student's T-test was used to determine differences in cell numbers in vivo and in vitro and in $H_2O_2$ concentrations in vitro. One-way ANOVA with Tukey's post-hoc test was used to assess differences in macrophages and nervous tissue sparing. Repeated measures ANOVA with Tukey's post hoc test determined differences in functional performances. Differences between groups were considered significant when P<0.05.

Example 10

Figure 19B:
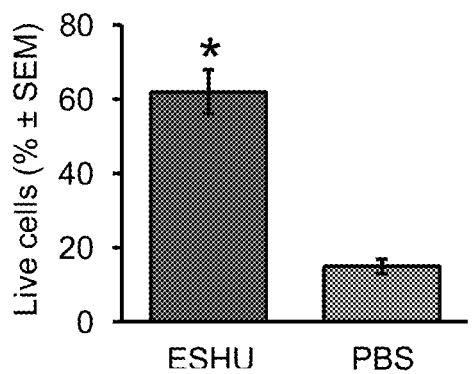
Figure 19C:
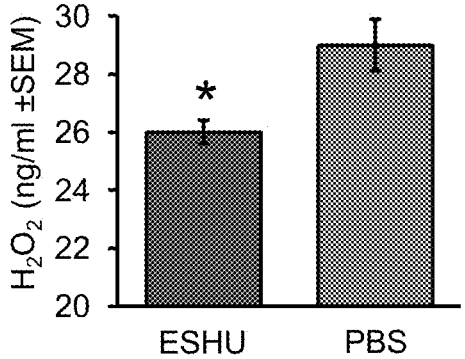
Figure 22E:
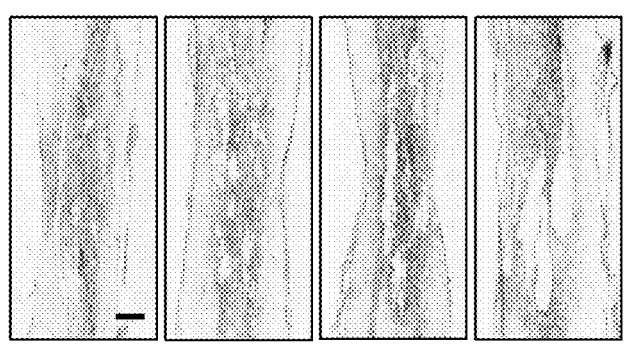
Figure 22E:
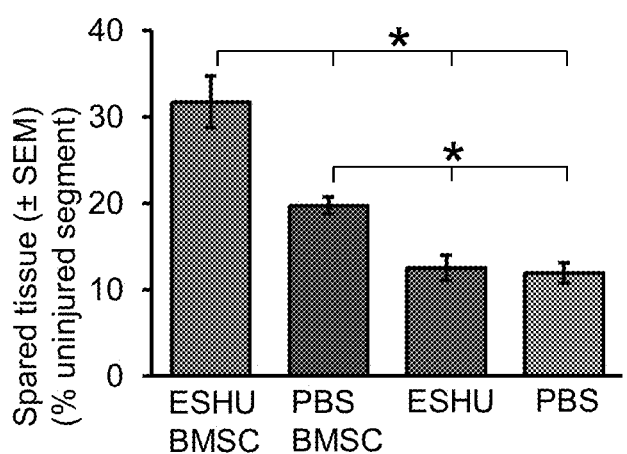

ESHU Protects BMSCs from Oxidative Stress-Induced Death and has Antioxidant Capabilities In Vitro It was tested whether ESHU protects cells from $H_2O_2$-mediated oxidative stress in vitro and found that BMSC survival was increased four-fold in ESHU (62±6%, SEM) compared with PBS (15±2%; FIG. 19B; P<0.05). To explore ESHU's cell protective effect we assessed its proficiency in scavenging $H_2O_2$. It was found that ESHU decreased the amount of $H_2O_2$ by 10% (3 ng/ml) in 30 min compared with PBS (FIG. 19C; P<0.05), suggesting ESHU-mediated oxidation of $H_2O_2$. The data show that ESHU exerts ROS scavenging (antioxidant) actions and protects against oxidative stress-mediated cell death.

Example 11

ESHU Promotes BMSC Transplant Survival in Damaged Nervous Tissue

It was investigated whether ESHU protects transplanted BMSCs from death in damaged nervous tissue using a spinal cord contusion model. At 15 min post-injection, rounded BMSCs were present in the injury when mixed in either ESHU (FIG. 20A) or PBS (FIG. 20B). One week post-injection, in both groups many spindle-shaped cells were also found (FIGS. 20C and 20D). The temporal morphological profile of the grafted cells is in accord with earlier observations (Nandoe-Tewarie et al., 2009, supra). It was found that 73±17% (SEM) of transplanted cells had survived in ESHU while 21±8% survived in PBS (FIG. 20E), which represents a significant (P<0.05) 3.5-fold increase in survival in ESHU compared with PBS. At four weeks post-injection, in both groups <1% of the cells has survived in the injury site. The data show that ESHU does not affect BMSC transplant morphology and protects against early cytotoxicity resulting in prolonged transplant presence.

Example 12

ESHU does not Affect the Injury-Induced Macrophage Response

Macrophages invade damaged nervous tissue and contribute to cell death (Ritfeld et al., *Neuroreport* 21(3), 221-226 (2010); Kigerl et al., *Exp. Neurol.* 233(1), 333-341 (2012)). ESHU breakdown products could possibly carry negative charges and so affect macrophage presence (Brodbeck et al., *Cytokine* 18(6), 311-319 (2002)). The influence of macrophages on ESHU's protective capacity was tested by assessing their presence in the injury after injection of BMSCs in ESHU (FIG. 21A-C) or PBS (FIG. 21D-21F), or ESHU or PBS only. The results demonstrated similar macrophage presence between all groups at one (FIG. 21G) and four weeks post-injection, suggesting that ESHU is non-immunogenic. The data indicate that macrophages are not implicated in ESHU-mediated transplant survival.

Example 13

ESHU-Promoted BMSC Survival Leads to Enhanced Neuroprotection

Because BMSC transplant survival is associated with neuroprotection (Nandoe Tewarie et al., 2009, supra) it was assessed whether ESHU-promoted transplant survival rendered enhanced tissue sparing (FIGS. 22A-22D). The results demonstrated that the volume of spared tissue in rats with the transplant in ESHU is 66% larger (P<0.05) than in rats with the transplant in PBS at four weeks post-transplantation (FIG. 22E). ESHU only had no effect on spared tissue volume in the damaged area (FIG. 22E). The data indicate that increased survival of intraneural BMSC transplants early after injection enhances neuroprotection of nervous tissue.

Example 14

ESHU-Promoted Transplant Survival is Accompanied by Improved Motor Recovery

Figure 23A:
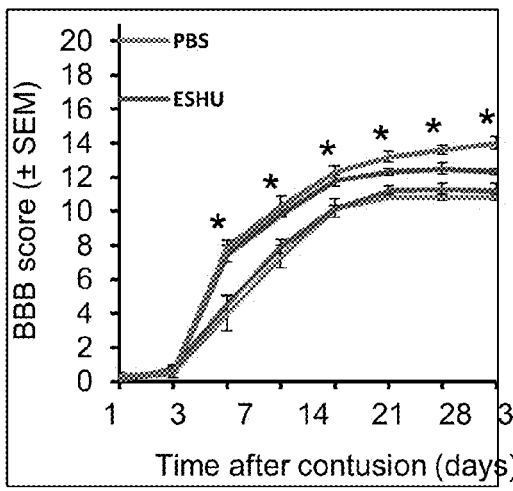
FIG. 23A-23D. ESHU leads to enhancement of motor function recovery by a bone marrow stromal cell transplant in the contused spinal cord. (A) Bar graph showing that overground walking ability, measured using the BBB scale, was significantly improved in rats with a bone marrow stromal cell (BMSC) transplant in ESHU compared with all other groups. Rats with BMSCs in PBS exhibited improved overground walking recovery compared with rats with ESHU or PBS alone. (B) Bar graph showing that the improvement in overground walking ability during the $4^{th}$-$6^{th}$ week post-injury was significantly improved in rats with a transplant in ESHU compared with all other groups. (C) Bar graph demonstrating the improved recovery in higher motor function in rats with the transplant in ESHU compared to PBS (asterisk, $p<0.05$). Rats in the other groups did not reach a high enough BBB score to assess the BBB sub-score. (D) Bar graph demonstrating the improved sensorimotor recovery in rats with the transplant in ESHU over all other groups (asterisk, $p<0.05$) and in rats with BMSCs in PBS over the control groups without BMSCs (number sign, $p<0.05$). Error bars in all bar graphs display standard error of the mean (SEM).
Figure 23B:
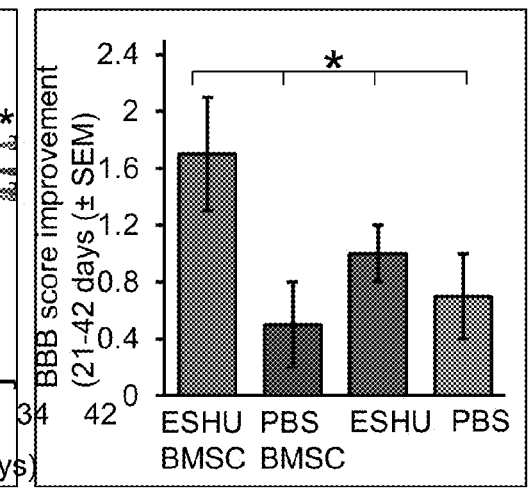
Figure 23C:
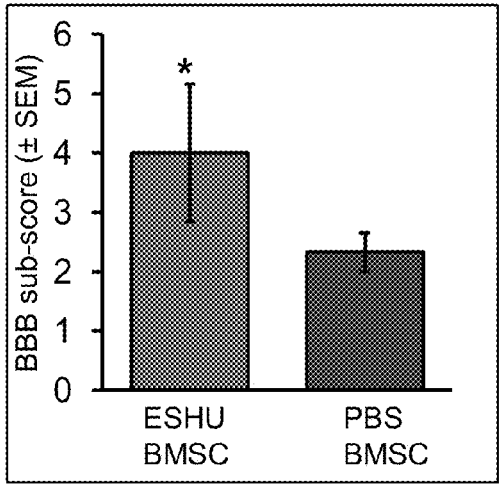
Figure 23D:
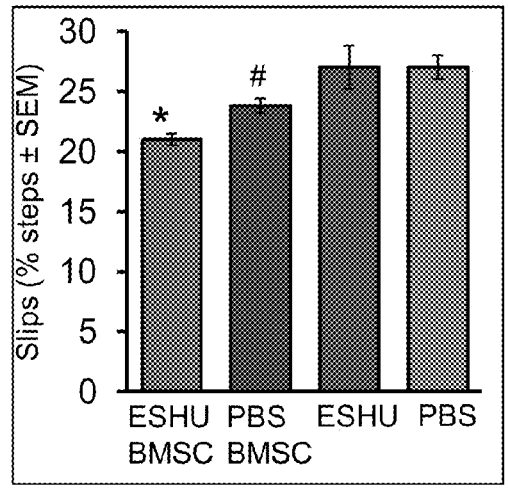

After spinal cord contusion, motor performance depends in part on the amount of nervous tissue at the injury site (Ritfeld et al., 2012, supra). It was examined whether augmented neuroprotection by BMSC transplants with ESHU-enhanced survival affected motor function recovery. Rats with the transplant in ESHU performed significantly (P<0.05) better in overground walking than the other groups (FIG. 23A). Rats with BMSCs in ESHU showed consistent (>95%) weight-supported plantar steps with frontlimb-hindlimb coordination. The control transplanted rats were less consistent (50-95%) making such steps, whereas rats with ESHU or PBS only were less consistent and lacked frontlimb-hindlimb coordination. During the $4^{th}$-$6^{th}$ week after injection, overground walking was increased by 1.7±0.4 points on the BBB scale in rats with the transplant in ESHU which was significantly (p<0.05) higher than the increase in the other groups (FIG. 23B. Higher motor functions of the hindlimbs were significantly improved (P<0.05) by 74% in rats with BMSC in ESHU compared with BMSCs in PBS (FIG. 23C). Rats that received ESHU or PBS did not reach a BBB score high enough to assess the BBB sub-score. Sensorimotor function was significantly increased (P<0.05) in rats with the transplant in ESHU compared with the other three groups (FIG. 23D). Rats receiving the transplant in PBS had significantly improved sensorimotor function compared with rats with ESHU or PBS alone (FIG. 23D).

The results showed that that ESHU, a synthetic injectable reverse thermal gel with antioxidant capability, protected transplanted BMSCs from death thereby prolonging their presence in damaged nervous tissue leading to enhanced nervous tissue sparing associated with improved motor function recovery. It was demonstrated that improved intraneural BMSC transplant survival enhances the overall therapeutic efficacy, which may have widespread impact on cell-based therapies for tissue repair.

$H_2O_2$ was used to determine the scavenging capability of ESHU, which is likely exerted through urethane groups (Christenson, et al., *J. Biomed. Mater. Res. A* 70(2), 245-255 (2004); Schubert et al., *J. Biomed. Mater. Res. A* 29(3), 337-347 (1995).

$H_2O_2$ is amply present in damaged nervous tissue (Moon et al., *J. Neurosci. Res.* 90(1), 243-256 (2012)). A 16% ESHU solution removed 3 ng $H_2O_2$ in a 30 min time period. Assuming continuous activity at 3 ng/30 min, ESHU removed ~20% of added $H_2O_2$ in the in vitro assay of ESHU's ability to protect BMSCs, which elicited a 47% increase in their survival relative to PBS. ESHU's protective effect could be increased using higher concentrations causing greater antioxidant capacity (Wu et al., *Cent. Nerv. Syst. Agents Med. Chem.* 12(2), 122-130 (2012)).

The in vitro demonstration of ESHU-induced protection against ROS-mediated cell death was translated to the in vivo model of nervous tissue damage. ESHU promoted transplant survival in a spinal cord contusion thereby prolonging their presence within the injury. Typically, after the primary insult, the site of tissue damage develops into a cytotoxic environment due in part to the accrual of ROS which contributes to the characteristic secondary loss of nervous tissue (Deng et al., *Prog. Brain Res.* 137, 37-47 (2002); Beattie et al., *Prog. Brain Res.* 137, 37-47 (2002)). Repair of tissue using antioxidant-based approaches can elicit neuroprotection (Bains and Hall, *Biochim. Biophys. Acta* 1822(5), 675-684 (2012)) which can be the first line of defense against the consequences of brain and spinal cord trauma (Hill, et al., *Eur. J. Neurosci.* 26(6), 1433-1445 (2007)).

Cell transplants survive poorly in damaged nervous tissue (Nandoe Tewarie, R. D. et al., 2009, supra; Swanger et al., *Cell Transplant.* 14(10), 775-786 (2005); Parr, et al., *Surg. Neurol.* 70 (6): 600-607 (2008); Hill et al., *Eur. J. Neurosci.* 26(6), 1433-1445 (2007)). In a spinal cord contusion model, loss of grafted cells mostly occurs during the first days post-injection (Nandoe Tewarie, R. D. et al., 2009, supra; Swanger et al., 005, supra; Parr, et al., 2008, supra; Hill et al., 2007, supra). 17β-estradiol, which augments the natural antioxidant defense (Pajović and Saici ć, *Physiol. Res.* 57(6), 801-811 (2008)) promotes survival of intraspinal Schwann cell transplants (Siriphorn et al., *J. Neurochem.* 115(4), 864-872 (2010)) confirming that ROS affect intraneural transplant survival. The antioxidant gel, ESHU protected transplants in damaged spinal cord tissue during the first week post-injection. Without being bound by theory, ESHU could affect survival by attenuating death-promoting pathways limiting apoptosis and/or promoting survival-promoting pathways. The latter may occur if ESHU served as a matrix for attachment of the anchorage-dependent BMSCs which would limit anoikis (Yu et al., *Stem Cells* 30(5), 956-964 (2012)).

Without being bound by theory, ESHU breakdown products could carry negative charges preventing adhesion of macrophages (Brodbeck, et al., *Cytokine* 18(6), 311-319 (2002)) and so limit their contribution to death of neural and transplanted cells (Swanger et al., *Cell Transplant.* 14(10), 775-786 (2005); Ritfeld, G. J. et al., *Neuroreport* 21(3), 221-226 (2010); Kigerl, K. A. et al. *Exp. Neurol.* 233(1), 333-341 (2012)). The number of macrophages was similar with or without the presence of ESHU. BMSCs are hypoimmunogenic, lacking MHC class II and co-stimulatory molecules for effector T cell induction (Nauta and Fibbe, *Blood* 110(10), 3499-3506 (2007)), and suppress T cell proliferation (Di Nicola, M. et al., *Blood* 99(10), 3838-3843 (2002)) thus the adaptive immune response is unlikely to be largely involved in allogeneic BMSC death. The data indicate that the protective effects of ESHU result from direct effects on the transplant rather than indirect effects involving macrophages.

The ESHU-mediated increase in BMSC survival in the damaged nervous tissue resulted in anatomical (tissue sparing) and functional (motor) improvements. Spared tissue volume was not affected by ESHU alone, indicating that the neuroprotection was elicited by the increased survival of the transplant. BMSC transplants result in greater volumes of spared tissue in a contused spinal cord segment, which was correlated with their survival and larger with shorter injury-transplantation intervals (Nandoe Tewarie et al., 2009, supra). These data suggested that the therapeutic window for BMSC-mediated neuroprotection can be in the first week post-injury. The results demonstrate that the efficacy of an intraspinal BMSC transplant to elicit neuroprotection depends on its degree of survival and that increased survival during the first week post-injury leads to increased spared tissue volumes.

Neuroprotection by intraneural BMSC transplants is thought to result from secreted growth factors, such as brain-derived neurotrophic factor and nerve growth factor and exerting paracrine effects on adjacent nervous tissue (Chen, Q., et al., *J. Neurosci. Res.* 80, 611-619) (2005); Li and Chopp, *Neurosci. Lett.* 456(3), 120-123 (2009)). Without being bound by theory, the finding that increased transplant survival results in increased tissue sparing could imply that the magnitude of neuroprotection elicited by the transplants depends on the concentration and/or availability of secreted growth factors.

Motor function of paralyzed hindlimbs was improved in rats that received the transplant in ESHU compared with the other groups. The improvements in overground walking (as measured with the BBB test) were particularly evident during the second half of the 6-weeks period. At six weeks after treatment, higher motor functions and sensorimotor function were also improved in rats that received BMSCs in ESHU over all other groups.

BMSC transplants result in improved motor function recovery after spinal cord and brain injury (see, for example, Hofstetter et al., *Proc. Natl. Acad. Sci. U.S.A.* 99(4), 2199-2204 (2002); Li and Chop, 2009, supra), which is typically correlated with the amount of spared nervous tissue (Bonilla C. et al., *J. Trauma Acute Care Surg.* 72(5), 1203-1212 (2012). Neuroprotection elicited by transplants with ESHU-increased survival likely contributes to the observed improved motor function recovery. Thus, the therapeutic efficacy of a BMSC transplant was enhanced by promoting survival. ESHU's ability to gel at body temperature allows for injection (i.e., minimally invasive) into closed injuries. Besides reducing oxidative stress and serving as a matrix for cells, ESHU can also be used to deliver drugs and/or functionalized with bioactive molecules to affect targeted biological events. Thus, ESHU is an important component in therapies for the traumatized or degenerated nervous system.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for increasing cell survival in a subject, comprising administering to a subject a therapeutically effective amount of a cell; and administering to the subject a therapeutically effective amount of a reverse thermal gel composition comprising a triblock copolymer, or a pharmaceutically acceptable salt thereof, having the structure B-A-B in which A is one of a polyurethane or a poly(ester urethane) group that comprises one or more pendant amine groups, blocked amine groups or active agents and B is a hydrophilic block, wherein the composition gels between 25° C. to 40° C. and is a liquid solution at a lower temperature, and wherein A is a copolymer of a diol and a diisocyanate, thereby increasing the survival of the cell in the subject.

2. The method of claim 1, wherein the cell is a mesenchymal stem cell or a bone marrow stromal cell.

3. The method of claim 1, wherein the subject has a neurodegenerative disorder, a stroke or a spinal cord injury.

4. The method of claim 3, comprising administering a therapeutically effective amount of the mesenchymal cell and the reverse thermal gel composition to the central nervous system or the peripheral nervous system.

5. The method of claim 4, comprising administering the cell and the reverse thermal gel composition in an intraneural transplant.

6. The method of claim 1, wherein the diol is an amino-substituted or N-substituted serinol in which the N is substituted with one of a hydrogen, a protective group, or an active agent.

7. The method of claim 6, wherein the N of the N-substituted serinol is —NHR in which R is a protective group.

8. The method of claim 7, wherein R is selected from the group consisting of carbobenzyloxy; p-methoxybenzyl carbonyl; tert-butyloxycarbonyl; 9-fluorenylmethyloxycarbonyl; benzyl; p-methoxybenzyl; 3,4-dimethoxybenzyl; p-methoxyphenyl; tosyl; nosyl (4-nitrobenzenesulfonyl) and 2-nitrobenzenesulfonyl.

9. The method of claim 1, wherein the diol comprises one or more ester groups, a pendant amino group or an amine.

10. The method of claim 9, wherein the diol is a reaction product of a cyclic anhydride and a diol comprising one or more pendant active groups, blocked active groups or active agents.

11. The method of claim 10, wherein the diol is the reaction product of succinic anhydride and the diol is an N-substituted serinol in which the N is substituted with one of a hydrogen, a protective group, or an active agent or wherein the diol is a polymer or an oligomer with terminal primary alcohol functional group ends.

12. The method of claim 6, wherein the diisocyanate is hexamethylene diisocyanate (1,6-diisocyanatohexane).

13. The method of claim 1, wherein the copolymer comprises the structure:

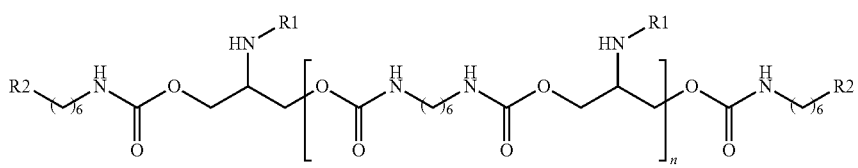

in which R1 is H or a protective group, R2 is isocyanate or —NC(O)-polyethylene glycol (—NC(O)—PEG) and n is greater than 5, 8-30, 8-25 or 18-30.

14. The method of claim 1, wherein the copolymer comprises the structure:

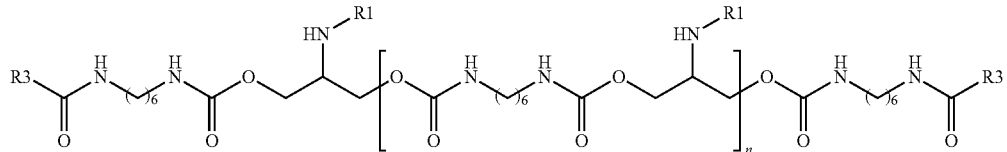

in which R1 is H or a protective group, R3 is PEG and n is greater than 5, 8-30, 8-25 or 18-30.

15. The method of claim 1, wherein the copolymer comprises the structure:

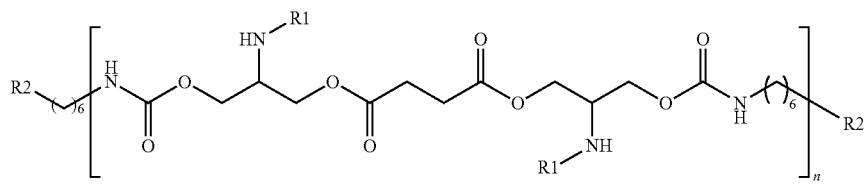

in which R1 is H or a protective group or an active agent, R2 is isocyanate or —NC(O)—PEG and n is greater than 5, 8-30, 8-25 or 18-30.

16. The method of claim 1, wherein the copolymer comprises the structure:

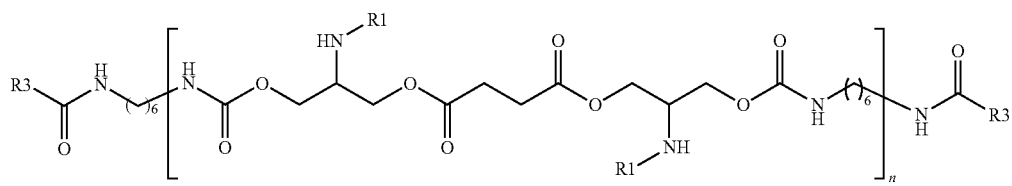

in which R1 is H or a protective group, R3 is PEG and n is greater than 5, 8-30, 8-25 or 18-30.

17. The method of claim 1, wherein the triblock copolymer has an average molecular weight of between about 5,000 and 10,000 Da (Daltons), excluding, when present, the molecular weight of the active agent.

18. The method of claim 1, wherein A is one of a polyurethane or poly(ester urethane) group that comprises one or more pendant charged or active groups.

19. The method of claim 18, wherein the one or more pendant charged or active groups is —NH$_2$.

20. The method of claim 1, wherein an active agent is complexed to the triblock copolymer.

21. The method of claim 1, wherein B is selected from the group consisting of polyethylene glycol (PEG), hyaluronan, poly(vinyl alcohol), oligo(vinyl alcohol), a poly(electrolyte), an oligo(electrolyte) and a polycarbohydrate.

22. The method of claim 1, wherein the reverse thermal gel composition comprises poly(ethylene glycol)-poly(serinol hexamethylene urethane).

23. A method for increasing survival of a transplanted cell in a subject, comprising
transplanting into a subject a therapeutically effective amount of a cell; and
administering to the subject an effective amount of poly(ethylene glycol)-poly(serinol hexamethylene urethane),
thereby increasing the survival of the transplanted cell in the subject.

24. The method of claim 23, wherein the cell is a mesenchymal stem cell, a bone marrow stem cell, stem cell, or a Schwann cell.

25. The method of claim 23, wherein the subject has a neurodegenerative disorder, a stroke or a spinal cord injury.

26. The method of claim 23, comprising administering the therapeutically effective amount of the mesenchymal cell and the effective amount of poly(ethylene glycol)-poly(serinol hexamethylene urethane) to the central nervous system or the peripheral nervous system.

27. The method of claim 23, comprising administering the mesenchymal cell and the poly(ethylene glycol)-poly(serinol hexamethylene urethane) in an intraneural transplant.

28. The method of claim 23, wherein increasing the survival of the cell comprises decreasing the production of reactive oxygen species.

29. A method of treating a subject with a spinal cord injury, stroke, or a neurodegenerative disorder, comprising administering to a subject a therapeutically effective amount of a cell; and administering to the subject a therapeutically effective amount of a reverse thermal gel composition comprising a triblock copolymer, or a pharmaceutically acceptable salt thereof, having the structure B-A-B in which A is one of a polyurethane or poly(ester urethane) group that comprises one or more pendant amine groups, blocked amine groups or active agents and B is a hydrophilic block, wherein the composition is a gel at 35° C. to 40° C. and a liquid solution at a lower temperature, and wherein A is a copolymer of a diol and a diisocyanate, thereby treating the spinal cord injury, stroke, or the neurodegenerative disorder.

30. The method of claim 29, wherein the reverse thermal gel composition comprises an effective amount of poly(ethylene glycol)-poly(serinol hexamethylene urethane).

31. The method of claim 29, further comprising administering the subject a therapeutically effective amount of a nerve growth factor.

* * * * *